(12) United States Patent
Brown et al.

(10) Patent No.: US 8,598,220 B2
(45) Date of Patent: Dec. 3, 2013

(54) ANTAGONISTS OF THE VANILLOID RECEPTOR SUBTYPE 1 (VR1) AND USES THEREOF

(75) Inventors: Brian S. Brown, Evanston, IL (US); John R. Koenig, Chicago, IL (US); Arthur R. Gomtsyan, Vernon Hills, IL (US); Chih-Hung Lee, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 790 days.

(21) Appl. No.: 12/474,035

(22) Filed: May 28, 2009

(65) Prior Publication Data

US 2009/0233953 A1    Sep. 17, 2009

Related U.S. Application Data

(62) Division of application No. 11/735,074, filed on Apr. 13, 2007, now Pat. No. 7,622,493.

(60) Provisional application No. 60/792,699, filed on Apr. 18, 2006.

(51) Int. Cl.
*A61K 31/416* (2006.01)
*C07D 231/56* (2006.01)

(52) U.S. Cl.
USPC ............. 514/406; 548/360.1; 548/362.5; 514/403

(58) Field of Classification Search
USPC .......... 548/360.1, 361.1, 362.5; 514/403, 406
See application file for complete search history.

(56) References Cited

U.S. PATENT DOCUMENTS

| 5,374,643 | A | 12/1994 | Atwal et al. | |
|---|---|---|---|---|
| 7,504,520 | B2 * | 3/2009 | Gomtsyan et al. | 548/469 |
| 7,507,761 | B2 | 3/2009 | Sebille et al. | |
| 7,615,570 | B2 * | 11/2009 | Brown et al. | 514/373 |
| 7,622,493 | B2 * | 11/2009 | Brown et al. | 514/406 |
| 2006/0128689 | A1 | 6/2006 | Gomtsyan et al. | |

FOREIGN PATENT DOCUMENTS

| WO | WO-03097586 A1 | 11/2003 |
|---|---|---|
| WO | WO-2004078744 A3 | 9/2004 |
| WO | 2005/075463 A1 | 8/2005 |
| WO | WO-2007042906 A1 | 4/2007 |
| WO | WO-2007050732 A1 | 5/2007 |
| WO | WO-2008110863 A1 | 9/2008 |

OTHER PUBLICATIONS

Bognar rerso et al., "Flavanoids XII. Synthesis of 4-ureldoflavan and bis (4flavanyl) urea," ACTS CHIM ACAD. SCI, 1963, 223-224, vol. 35.
Caterina et al., "Impaired Nociception and Pain Sensation in Mice Lacking the Capsaicin Receptor," Science, 2000, 306-313, vol. 288.
Caterina et al., "The Vanilloid Receptor: A Molecular Gateway to the Pain Pathway," Annu Rev Neurosci, 2001, 487-517, vol. 24.
Caterina M.J. et al., "The Capsaicin Receptor: A Heat-Activated Ion Channel in the Pain Pathway," (Binary/Image), 1997, 816-824, vol. 389.
Collier et al., "The abdominal constriction response and its suppression by analgesic drugs in the mouse," Br J Pharmac Chemother, 1968, 295-310, vol. 32.
Dade, J. "Synthesis of 2-Substituted Trifluoromethylquinolines for the Evaluation of Leishmanicidal Activity", Chem Pharm Bull 2001, vol. 49—Issue 4, 480-483.
Database Beilstein Beilstein Institute for Organic Chemistry, Frank Furt-Main, DE; XP002507218 Database accession No. brn 355828 abstract & Webster et al: J.Chem.Soc., 1965, pp. 4785-4789.
Davis et al., "Vanilloid receptor-1 is essential for inflammatory thermal hyperalgesia," (Binary/Image), 2000, 183-187, vol. 405.
Fowler, C. "Intravesical Treatment of Overactive Bladder," Urology, 2000, 60-64, vol. 55.
Hayes et al., "Cloning and Functional Expression of a Human Orthologue of Rat Vanilloid Receptor-1," (Binary/Image), 2000, 205-215, vol. 88.
International Search Report for application No. PCT/US05/042545, Mailed on Feb. 19, 2009, 3 pages.
International Search Report for application No. PCT/US2007/0066515, Mailed on Sep. 15, 2000, 3 pages.
Nolano et al., "Topical Capsaicin in Humans: Parallel Loss of Epidermal Nerve Fibers and Pain Sensation," (Binary/Image), 1999, 135-145, vol. 81.
Patani et al., "Bioisosterism: A Rational Approach in Drug Design", Chemical Reviews, 1996, vol. 96, 3147-3176.
Pircio, A.W. et al., "A New Method for the Evaluation of Analgesic Activity Using Adjuvant-Induced Arthritis in the Rat," Eur Journal of Pharmacology, 1975, 207-215, vol. 31.
Honore, et al., Pharmacol. Exp. Ther. 2005, 314(1), pp. 410-421.
Drizin, et al., Bioorg. Med. Chem. 2006, 14, pp. 4740-4749.
Supplementary European Search Report from European Patent Application Publication No. EP2012778, dated Jul. 5, 2011.

* cited by examiner

*Primary Examiner* — Golam M M Shameem

(57) ABSTRACT

The present invention is directed to compounds of formula (I)

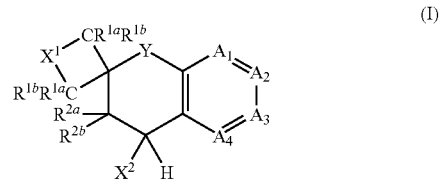

(I)

wherein variables $X^1$, $X^2$, Y, $R^{1a}$, $R^{1b}$, $R^{2a}$, $R^{2b}$, $A_1$, $A_2$, $A_3$, and $A_4$ are as defined in the description, and methods of use to treat pain, neuropathic pain, allodynia, pain associated with inflammation or an inflammatory disease, inflammatory hyperalgesia, bladder overactivity, and urinary incontinence.

5 Claims, No Drawings

ANTAGONISTS OF THE VANILLOID RECEPTOR SUBTYPE 1 (VR1) AND USES THEREOF

This application is a divisional of U.S. Non-Provisional patent application Ser. No. 11/735,074, filed on Apr. 13, 2007, which seeks priority from U.S. Provisional Patent Application Ser. No. 60/792,699, filed Apr. 18, 2006, which is hereby incorporated by reference in its entirety.

FIELD OF INVENTION

The present invention relates to spirochromane compounds of formula (I), which are useful for treating disorders caused by or exacerbated by vanilloid receptor type 1 (VR1) activity. The present invention also includes pharmaceutical compositions containing compounds of formula (I) and methods for treating several types of pain, bladder overactivity, and urinary incontinence using said compounds and said pharmaceutical compositions.

BACKGROUND OF INVENTION

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effects of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (−/−) mice also did not show reduced sensitivity to nerve injury-induced mechanical or thermal nociception. However, the VR1 knock-out mice were insensitive to the noxious effects of intradermal capsaicin, exposure to intense heat (50-55° C.), and failed to develop thermal hyperalgesia following the intradermal administration of carrageenan.

The compounds of the present invention are novel VR1 antagonists and have utility in treating disorders caused by or exacerbated by vanilloid receptor type 1 (VR1) activity, for example pain, neuropathic pain, allodynia, pain associated with inflammation or an inflammatory disease, inflammatory hyperalgesia, bladder overactivity, and urinary incontinence.

DETAILED DESCRIPTION OF THE INVENTION

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylbutyl, 3-methylhexyl, 3,3-dimethylbutyl, 2,2-dimethylpentyl, 2,3-dimethylpentyl, n-heptyl, n-octyl, n-nonyl, and n-decyl.

The term "alkynyl" as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aryl" as used herein, means a phenyl group, a bicyclic aryl or a tricyclic aryl. The bicyclic aryl or the tricyclic aryl is a hydrocarbon fused ring system containing zero heteroatom wherein one or more of the fused rings is a phenyl group. Bicyclic aryl is a phenyl group fused to a monocyclic cycloalkyl group, as defined herein, a monocyclic cycloalkenyl group, as defined herein, or another phenyl group. Tricyclic aryl is a bicyclic aryl fused to a monocyclic cycloalkyl group, as defined herein, a monocyclic cycloalkenyl group, as defined herein, or another phenyl group. The phenyl group, the bicyclic aryls and the tricyclic aryls of the present invention are appended to the parent moiety through any substitutable atoms in the phenyl group, the bicyclic aryls and the tricyclic aryls respectively. The phenyl group, the bicyclic aryls and the tricyclic aryls of the present invention can be unsubstituted or substituted. Representative examples of aryl include, but are not limited to, anthracenyl, fluorenyl, 2,3-dihydro-1H-inden-1-yl, 2,3-dihydro-1H-inden-4-yl, inden-1-yl, inden-4-yl, naphthyl, phenyl, 5,6,7,8-tetrahydronaphthalen-1-yl, 1,2,3,4-tetrahydronaphthalen-2-yl and tetrahydronaphthyl.

The term "cycloalkyl" or "cycloalkane" as used herein, means a monocyclic cycloalkyl or a bicyclic cycloalkyl. The monocyclic cycloalkyl is a saturated hydrocarbon ring system having three to eight carbon atoms and zero heteroatom. Examples of monocyclic cycloalkyls include cyclopropyl, cyclobutyl, cyclopentyl, cyclohexyl, cycloheptyl, and cyclooctyl. The bicyclic cycloalkyl is a fused ring system wherein the monocyclic cycloalkyl ring is fused to another monocyclic cycloalkyl group, as defined herein. The monocyclic cycloalkyls and the bicyclic cycloalkyls of the present invention can be unsubstituted or substituted, and are connected to the parent molecula moiety through any substitutable carbon atom of the monocyclic cycloalkyls and the bicyclic cycloalkyls respectively.

The term "cycloalkenyl" or "cycloalkene" as used herein, means a monocyclic cycloalkenyl or a bicyclic cycloalkenyl. The monocyclic cycloalkenyl is a non-aromatic, partially unsaturated hydrocarbon ring system, having 4, 5, 6, 7 or 8 carbon atoms and zero heteroatom. The 4-membered ring systems have one double bond, the 5- or 6-membered ring systems have one or two double bonds, and the 7- or 8-membered ring systems have one, two or three double bonds. Representative examples of monocyclic cycloalkenyl groups include, but not limited to, cyclobutenyl, cyclopentenyl, and cyclohexenyl. The bicyclic cycloalkenyl is a hydrocarbon fused ring system wherein the monocyclic cycloalkenyl ring is fused to a monocyclic cycloalkyl group, as defined herein, or another monocyclic cycloalkenyl group, as defined herein. Representative examples of the bicyclic cycloalkenyls include, but not limited to, azulenyl, 4,5,6,7-tetrahydro-3aH-indene, octahydronaphthalenyl and 1,6-dihydro-pentalene. The monocyclic cycloalkenyls and the bicyclic cycloalkenyls of the present invention can be unsubstituted or substituted, and are attached to the parent molecular moiety through any substitutable carbon atom of the monocyclic cycloalkenyls and the bicyclic cycloalkenyls respectively.

The term "halo" or "halogen" as used herein, means —Cl, —Br, —I or —F.

The term "haloalkoxy" as used herein, refers to an alkoxy group, as defined herein, in which one, two, three, four, five or six hydrogen atoms are replaced by halogen. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, refers to an alkyl group, as defined herein, in which one, two, three or four, five, or six hydrogen atoms are replaced by halogen. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, refers to a monocyclic heterocycle or a bicyclic heterocycle. The monocyclic heterocycle is a non-aromatic, saturated or partially unsaturated hydrocarbon ring system containing at least one heteroatom selected from the group consisting of oxygen, nitrogen and sulfur. Monocyclic ring systems are exemplified by a 4-membered ring containing three carbon atoms and one heteroatom selected from oxygen, nitrogen and sulfur, or a 5-, 6-, 7-, or 8-membered ring containing one, two, three or four heteroatoms wherein the heteroatoms are independently selected from nitrogen, oxygen and sulfur, and the remaining atoms are carbon atoms. The 5-membered ring has 0 or 1 double bond. The 6-membered ring has 0, 1 or 2 double bonds. The 7- or 8-membered ring has 0, 1, 2 or 3 double bonds. The monocyclic heterocycle of the present invention can be unsubstituted or substituted. Representative examples of unsubstituted and substituted monocyclic ring systems include, but not limited to, azetidinyl, azepanyl, azepinyl, diazepinyl, dioxolanyl, dioxanyl, dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, 2-oxo-oxazolinyl, oxazolidinyl, piperazinyl, piperidinyl (piperidyl), pyranyl, pyrazolinyl, pyrazolidinyl, pyrrolinyl, pyrrolidinyl, tetrahydrofuryl, tetrahydropyranyl, tetrahydropyridyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, 1,4-diazepanyl and trithianyl. Bicyclic heterocycle is a monocyclic heterocycle fused to a phenyl group, a monocyclic cycloalkenyl group, as defined herein, a monocyclic cycloalkyl group, as defined herein, or a monocyclic heterocycle group. The bicyclic heterocycles of the present invention can be unsubstituted or substituted. Representative examples of bicyclic heterocycles include but are not limited to, benzodioxinyl, benzopyranyl, benzothiopyranyl, 2,3-dihydroindolyl, indolizinyl, tetrahydroisoquinolinyl, tetrahydroquinolinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, and octahydropyrrolo[3,4-c]pyrrolyl. The monocyclic heterocycles and the bicyclic heterocycles of the present invention are connected to the parent molecular moiety through any substitutable carbon or nitrogen atom in the monocyclic heterocycles and the bicyclic heterocycles respectively. The nitrogen heteroatom may or may not be quaternized, and the nitrogen or sulfur heteroatom may or may not be oxidized. In addition, the nitrogen containing heterocyclic rings may or may not be N-protected.

The term "heteroaryl" as used herein, means a monocyclic heteroaryl or a bicyclic heteroaryl. The monocyclic heteroaryl is an aromatic, five- or six-membered ring where at least one atom is selected from the group consisting of N, O, and S, and the remaining atoms are carbon. The five membered rings have two double bonds, and the six membered rings have three double bonds. The bicyclic heteroaryl is a monocyclic heteroaryl fused to a phenyl group, a monocyclic cycloalkyl, as defined herein, a monocyclic cycloalkenyl, as defined herein, a monocyclic heterocycle, as defined herein, or a monocyclic heteroaryl. Representative examples of monocyclic and bicyclic heteroaryls include, but not limited to, benzothienyl, benzoxazolyl, benzimidazolyl, benzoxadiazolyl, 6,7-dihydro-1,3-benzothiazolyl, furanyl (furyl), imidazolyl, imidazo[1,2-a]pyridinyl, indazolyl, indolyl, isoindolyl, isoxazolyl, isoquinolinyl, isothiazolyl, naphthyridinyl, oxadiazolyl, oxazolyl, pyridoimidazolyl, pyridyl, pyridazinyl, pyrimidinyl, pyrazinyl, pyrazolyl, pyrrolyl, quinolinyl, thiazolyl, thienyl, triazolyl, thiadiazolyl, tetrazolyl, 1,2,3,4-tetrahydro-1,8-naphthyridin-2-yl, and 5,6,7,8-tetrahydroquinolin-5-yl. The monocyclic and the bicyclic heteroaryls of the present invention can be substituted or unsubstituted, and are connected to the parent molecular moiety through any substitutable carbon or nitrogen atom in the monocyclic and the bicyclic heteroaryls respectively. In addition, the nitrogen heteroatom may or may not be quaternized, the nitrogen and the sulfur atoms in the group may or may not be oxidized. Also, the nitrogen containing rings may or may not be N-protected.

The term "heteroatom" as used herein, refers to nitrogen, oxygen and sulfur atoms.

The term "hydroxyalkyl" as used herein, means an alkyl group, as defined herein, wherein one or two hydrogen atoms are substituted by —OH. Representative examples of hydroxyalkyl include, but are not limited to, hydroxymethyl, 2-hydroxyethyl, 3-hydroxypropyl, 2,3-dihydroxypentyl and 2-ethyl-4-hydroxyheptyl.

The term "oxo" as used herein, means an =O group.

Preparation of Compounds of the Present Invention

The compounds of this invention can be prepared by a variety of synthetic procedures. Representative procedures are shown in, but are not limited to schemes 1, 2 and 3.

cinimidylcarbonate in a solvent such as, but not limited to, acetonitrile, dichloromethane, or tetrahydrofuran, at a temperature from about room temperature to about 50° C., for a period of about 2 hours to about 48 hours.

Treatment of compounds of formula (2) with amines of formula (3) in the presence of a base such as, but not limited to, diisopropylethylamine or triethylamine, in a solvent such as, but not limited to, N,N-dimethylformamide, affords ureas of formula (4). The reaction can be performed at a temperature from about room temperature to about 50° C., for a period of about 2 hours to about 24 hours.

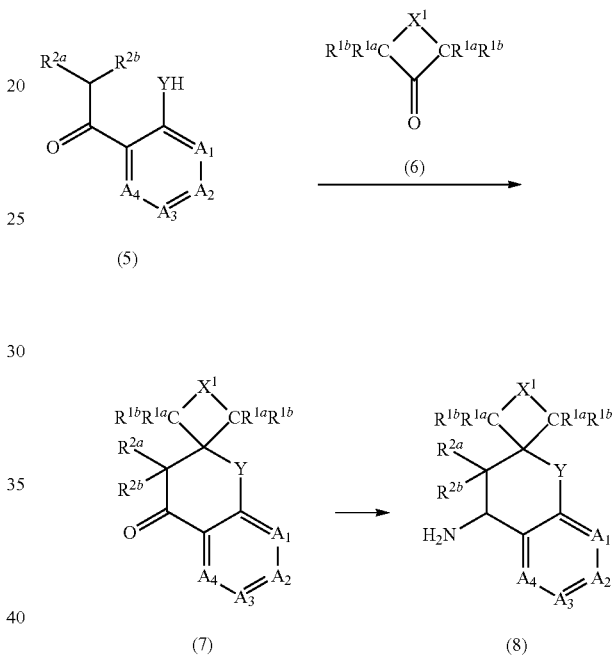

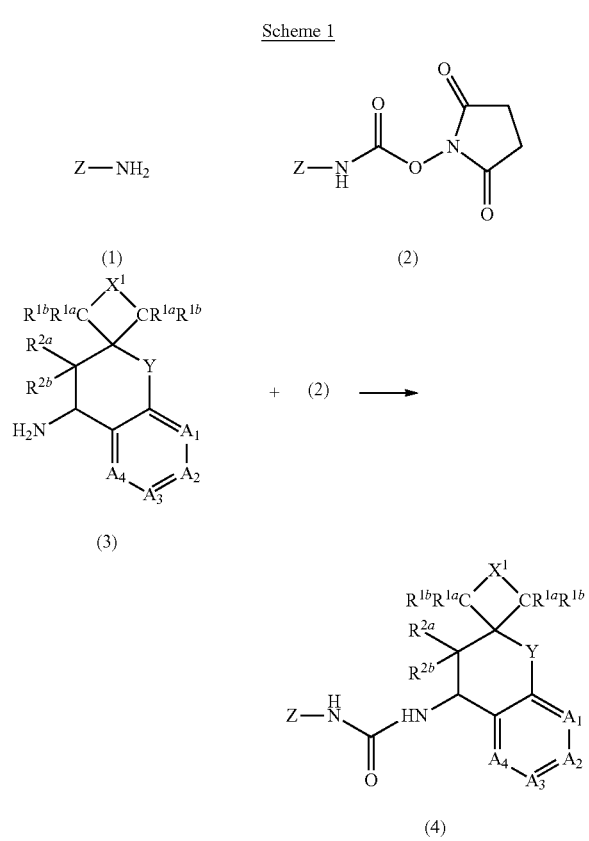

Ureas of formula (4) wherein $X^1$, Y, Z, $R^{1a}$, $R^{1b}$, $R^{2a}$, $R^{2b}$, $A_1$, $A_2$, $A_3$, $A_4$, are as defined in formula (I), can be prepared as shown in Scheme 1. Amines of formula (1) can be converted to compounds of formula (2) by reacting with disuc- Amines of formula (8) wherein Y is O, S, or $N(R^7)$, and $X^1$, $R^{1a}$, $R^{1b}$, $R^{2a}$, $R^{2b}$, $R^7$, $A_1$, $A_2$, $A_3$, $A_4$, are as defined in formula (I) can be prepared as shown in Scheme 2.

Compounds of formula (5), upon treatment with cyclic ketones of formula (6), in the presence of a base such as, but not limited to, pyrrolidine, provides ketones of formula (7). The reaction is generally facilitated in a solvent such as, but not limited to, toluene, at reflux.

Ketones of formula (7) can be converted to amines of formula (8) by (a) treating compounds of formula (7) with methoxylamine hydrochloride and a base such as, but not limited to, pyridine or triethylamine; and (b) treating the product of step (a) with a reducing agent.

Step (a) is generally conducted in an alcoholic solvent such as, but not limited to, methanol, at about room temperature to about 50° C., for a period of about 1 hour to about 10 hours.

Examples of the reducing agent used in step (b) include, but not limited to, hydrogen and 10% palladium/carbon under acidic condition, hydrogen/Raney-Nickel, and lithium aluminum hydride.

Scheme 3

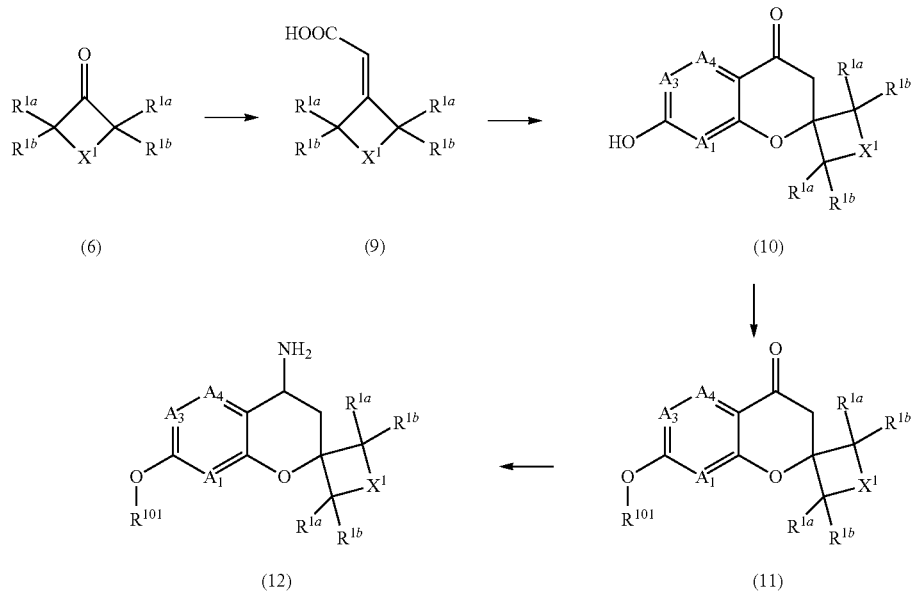

Amines of formula (12) wherein $X^1$, $R^{1a}$, $R^{1b}$, $A_1$, $A_3$, $A_4$, are as defined in formula (I) and $R^{101}$ is alkyl or $(R^{1a}R^{1b})_q$—$R_E$ wherein $R_E$, q, $R^{1a}$ and $R^{1b}$ are as defined in formula (I), can be prepared as shown in Scheme 3.

Cyclic ketones of formula (6) can be converted to compounds of formula (9) when treated with bromoacetic acid and diethyl phosphate, in the presence of a base such as, but not limited to, sodium hydride, in a solvent such as, but not limited to, 1,2-dimethoxyethane, at about room temperature.

Compounds of formula (9), upon treatment with phosphorous(III) oxy chloride and resorcinol, in the presence of zinc chloride, provide compounds of formula (10).

Alkylation of compounds of formula (10) can be achieved by, for example, treatment with an alkylating agent of formula $R^{101}$—X wherein X is a leaving group such as, but not limited to, Cl, Br, I, triflate or methanesulfonate, in the presence of a base such as, but not limited to, potassium carbonate or sodium hydride.

Compounds of formula (11) can be converted to compounds of formula (12) using the reaction conditions for the conversion of (7) to (8) as described in Scheme 2. It is understood that the schemes described herein are for illustrative purposes and that routine experimentation, including appropriate manipulation of the sequence of the synthetic route, protection of any chemical functionality that are not compatible with the reaction conditions and the removal of such protecting groups are included in the scope of the invention.

Compounds of the Present Invention

Compounds of the invention can have the formula (I) as described herein. More particularly, compounds of formula (I) can include, but are not limited to compounds wherein Y is selected from the group consisting of —S—, —S(O), —S(O)$_2$, —O—, —N($R^7$)— or —C($R^{1a}R^{1b}$)—, most preferably —O—. The invention includes compounds in which Y is O, $A_1$ is N; $A_2$ is N; $A_3$ is CR$^5$; and $A_4$ is CR$^6$, $X^1$ is —(CR$^{1a}$R$^{1b}$)$_m$—, and m can be 1, 2, 3, or 4. The invention includes compounds in which Y is O, $A_1$ is N; $A_2$ is N; $A_3$ is CR$^5$; and $A_4$ is CR$^6$, $X^1$ is —C(CR$^{1a}$R$^{1b}$)$_m$—, m can be 1, 2, 3, or 4, and $X^2$ is —N(H)C(O)N(H)—Z. Compounds of the invention are also those in which Y is O, $A_1$ is N; $A_2$ is N; $A_3$ is CR$^5$; and $A_4$ is CR$^6$, $X^1$ is —(CR$^{1a}$R$^{1b}$)$_m$—, m can be 1, 2, 3, or 4, and $X^2$ is —(CR$^g$R$^h$)$_q$—N(H)C(O)N(H)—Z. It is contemplated that for all the foregoing compounds $R^{1a}$, $R^{1b}$, $R^{2a}$, $R^{2b}$, $R^x$, $R^y$, $R^5$, $R^6$, $R_A$, $R_B$, $R_E$, $R^7$, Z, $R^g$ and $R^h$ are as described in claim 1

The present invention also includes compounds in which Y is O, $A_1$ is N; $A_2$ is N; $A_3$ is CR$^5$; and $A_4$ is CR$^6$, $X^1$ is —(CR$^{1a}$R$^{1b}$)$_n$G$^1$-, and n can be 1, 2, or 3. The present invention also includes compounds in which Y is O, $A_1$ is N; $A_2$ is N; $A_3$ is CR$^5$; and $A_4$ is CR$^6$, $X^1$ is —C(R$^{1a}$R$^{1b}$)$_m$—, n can be 1, 2, or 3; and $X^2$ is —N(H)C(O)N(H)—Z. Compounds included in the present invention are also those in which Y is O, $A_1$ is N; $A_2$ is N; $A_3$ is CR$^5$; and $A_4$ is CR$^6$, $X^1$ is —(CR$^{1a}$R$^{1b}$)$_n$G$^1$-, n can be 1, 2, or 3; and $X^2$ is —(CR$^g$R$^h$)$_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^5$, $R^6$, $R_A$, $R_B$, $R_E$, $R^7$, Z, $R^g$ and $R^h$ are as described in claim 1.

The present invention also includes compounds in which Y is O, $A_1$ is N; $A_2$ is N; $A_3$ is CR$^5$; and $A_4$ is CR$^6$, $X^1$ is —(CR$^{1a}$R$^{1b}$)$_p$-G$^1$-C(R$^{1a}$R$^{1b}$)—; and p can be 1 or 2. The present invention also includes compounds in which Y is O, $A_1$ is N; $A_2$ is N; $A_3$ is CR$^5$; $A_4$ is CR$^6$, $X^1$ is —(CR$^{1a}$R$^{1b}$)$_p$-G$^1$-C(R$^{1a}$R$^{1b}$)—; p is 1 or 2; and $X^2$ is —N(H)C(O)N(H)—Z. Compounds included in the present invention are also those in which Y is O, $A_1$ is N; $A_2$ is N; $A_3$ is CR$^5$; $A_4$ is CR$^6$, $X^1$ is C(R$^{1a}$R$^{1b}$)$_p$-G-C(R$^{1a}$R$^{1b}$)—; p is 1 or 2; and $X^2$ is —(CR$^g$R$^h$)$_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^5$, $R^6$, $R_A$, $R_B$, $R_E$, $R^7$, Z, $R^g$ and $R^h$ are as described in claim 1.

The invention includes compounds in which Y is O, $A_1$ is N; $A_2$ is CR$^4$; $A_3$ is N; and $A_4$ is CR$^6$, $X^1$ is —(CR$^{1a}$R$^{1b}$)$_m$—, and m can be 1, 2, 3, or 4. The invention includes compounds in which Y is O, $A_1$ is N; $A_2$ is CR$^4$; $A_3$ is N; and $A_4$ is CR$^6$, $X^1$ is —(CR$^{1a}$R$^{1b}$)$_m$—, m can be 1, 2, 3, or 4, and $X^2$ is —N(H) C(O)N(H)—Z. Compounds of the invention are also those in which Y is O, $A_1$ is N; $A_2$ is CR$^4$; $A_3$ is N; and $A_4$ is CR$^6$, $X^1$ is —(CR$^{1a}$R$^{1b}$)$_m$—, m can be 1, 2, 3, or 4, and $X^2$ is —(CR$^g$R$^h$)$_q$—N(H)C(O)N(H)—Z. It is contemplated that for all the foregoing compounds $R^{1a}$, $R^{1b}$, $R^{2a}$, $R^{2b}$, $R^x$, $R^y$, $R^4$, $R^6$, $R_A$, $R_B$, $R_E$, $R^7$, Z, $R^g$ and $R^h$ are as described in claim 1

The invention includes compounds in which Y is O, $A_1$ is N; $A_2$ is $CR^4$; $A_3$ is N; and $A_4$ is $CR^6$, $X^1$ is $-(CR^{1a}R^{1b})_n G^1-$, and n can be 1, 2, or 3. The invention includes compounds in which Y is O, $A_1$ is N; $A_2$ is $CR^4$; $A_3$ is N; and $A_4$ is $CR^6$, $X^1$ is $-(CR^{1a}R^{1b})_m-$, m can be 1, 2, 3, or 4, and $X^2$ is $-N(H)C(O)N(H)-Z$. Compounds of the invention are also those in which Y is O, $A_1$ is N; $A_2$ is $CR^4$; $A_3$ is N; and $A_4$ is $CR^6$, $X^1$ is $-(CR^{1a}R^{1b})_m-$, m can be 1, 2, 3, or 4, and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $G^1$, $R^4$, $R^6$, $R_A$, $R_B$, $R_E$, $R^7$, Z, $R^g$ and $R^h$ are as described in claim 1.

The invention includes compounds in which Y is O, $A_1$ is N; $A_2$ is $CR^4$; $A_3$ is N; and $A_4$ is $CR^6$, $X^1$ is $-(CR^{1a}R^{1b})_p-G^1-C(R^{1a}R^{1b})-$; -, and p can be 1 or 2. The invention includes compounds in which Y is O, $A_1$ is N; $A_2$ is $CR^4$; $A_3$ is N; and $A_4$ is $CR^6$, $X^1$ is $-(CR^{1a}R^{1b})_p-G^1-C(R^{1a}R^{1b})-$; p can be 1 or 2, and $X^2$ is $-N(H)C(O)N(H)-Z$. Compounds of the invention are also those in which Y is O, $A_1$ is N; $A_2$ is $CR^4$; $A_3$ is N; and $A_4$ is $CR^6$, $X^1$ is $-(CR^{1a}R^{1b})_p-G^1-C(R^{1a}R^{1b})-$, p can be 1 or 2, and $X^2$ is $-(CR^g R^h)_n-N(H)C(O)N(H)-Z$. It is contemplated that for all the foregoing compounds $R^{1a}$, $R^{1b}$, $R^{2a}$, $R^{2b}$, $R^x$, $R^y$, $R^4$, $R^6$, $R_A$, $R_B$, $R_E$, $R^7$, Z, $R^g$ and $R^h$ are as described in claim 1.

The invention includes compounds in which Y is O, $A_1$ is N; $A_2$ is $CR^4$; $A_3$ is $CR^5$; and $A_4$ is N, $X^1$ is $-(CR^{1a}R^{1b})_m-$, and m can be 1, 2, 3, or 4. The invention includes compounds in which Y is O, $A_1$ is N; $A_2$ is $CR^4$; $A_3$ is $CR^5$; and $A_4$ is N, $X^1$ is $-(CR^{1a}R^{1b})_m-$, m can be 1, 2, 3, or 4, and $X^2$ is $-N(H)C(O)N(H)-Z$. Compounds of the invention are also those in which Y is O, $A_1$ is N; $A_2$ is $CR^4$; $A_3$ is $CR^5$; and $A_4$ is N, $X^1$ is $-(CR^{1a}R^{1b})_m-$, m can be 1, 2, 3, or 4, and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $R^4$, $R^5$, $R_A$, $R_B$, $R_E$, $R^7$, Z, $R^g$ and $R^h$ are as described in claim 1

The present invention also includes compounds in which Y is O, $A_1$ is N; $A_2$ is $CR^4$; $A_3$ is $CR^5$; and $A_4$ is N, $X^1$ is $-(CR^{1a}R^{1b})_n G^1-$, and n can be 1, 2, or 3. The present invention also includes compounds in which Y is O, $A_1$ is N; $A_2$ is $CR^4$; $A_3$ is $CR^5$; and $A_4$ is N, $X^1$ is $-(CR^{1a}R^{1b})_n G^1-$, n can be 1, 2, or 3; and $X^2$ is $-N(H)C(O)N(H)-Z$. Compounds included in the present invention are also those in which Y is O, $A_1$ is N; $A_2$ is $CR^4$; $A_3$ is $CR^5$; and $A_4$ is N, $X^1$ is $-(CR^{1a}R^{1b})_p-G^1-$, n can be 1, 2, or 3; and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $G^1$, $R^4$, $R^5$, $R_A$, $R_B$, $R_E$, $R^7$, Z, $R^g$ and $R^h$ are as described in claim 1.

The present invention also includes compounds in which Y is O, $A_1$ is N; $A_2$ is $CR^4$; $A_3$ is $CR^5$; and $A_4$ is N, $X^1$ is $-(CR^{1a}R^{1b})_n-G^1-C(R^{1a}R^{1b})-$; and p can be 1 or 2. The present invention also includes compounds in which Y is O, $A_1$ is N; $A_2$ is $CR^4$; $A_3$ is $CR^5$; $A_4$ is N, $X^1$ is $-(CR^{1a}R^{1b})_p-G-C(R^{1a}R^{1b})-$; p is 1 or 2; and $X^2$ is $-N(H)C(O)N(H)-Z$ Compounds included in the present invention are also those in which Y is O, $A_1$ is N; $A_2$ is $CR^4$; $A_3$ is $CR^5$; $A_4$ is N, $X^1$ is $-(CR^{1a}R^{1b})_p-G^1-C(R^{1a}R^{1b})-$; p is 1 or 2; and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $G^1$, $R^4$, $R^5$, $R_A$, $R_B$, $R_E$, $R^7$, Z, $R^g$ and $R^h$ are as described in claim 1.

The invention includes compounds in which Y is O, $A_1$ is $CR^3$; $A_2$ is N; $A_3$ is N; and $A_4$ is $CR^6$, $X^1$ is $-(CR^{1a}R^{1b})_m-$, and m can be 1, 2, 3, or 4. The invention includes compounds in which Y is O, $A_1$ is $CR^3$; $A_2$ is N; $A_3$ is N; and $A_4$ is $CR^6$, $X^1$ is $-(CR^{1a}R^{1b})_m-$, m can be 1, 2, 3, or 4, and $X^2$ is $-N(H)C(O)N(H)-Z$. Compounds of the invention are also those in which Y is O, $A_1$ is $CR^3$; $A_2$ is N; $A_3$ is N; and $A_4$ is $CR^6$, $X^1$ is $-(CR^{1a}R^{1b})_m-$, m can be 1, 2, 3, or 4, and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $R^3$, $R^6$, $R_A$, $R_B$, $R_E$, $R^7$, Z, $R^g$ and $R^h$ are as described in claim 1

The present invention also includes compounds in which Y is O, $A_1$ is $CR^3$; $A_2$ is N; $A_3$ is N; and $A_4$ is $CR^6$, $X^1$ is $-(CR^{1a}R^{1b})_n G^1-$, and n can be 1, 2, or 3. The present invention also includes compounds in which Y is O, $A_1$ is $CR^3$; $A_2$ is N; $A_3$ is N; and $A_4$ is $CR^6$, $X^1$ is $-(CR^{1a}R^{1b})_n G-$, n can be 1, 2, or 3; and $X^2$ is $-N(H)C(O)N(H)-Z$. Compounds included in the present invention are also those in which Y is O, $A_1$ is $CR^3$; $A_2$ is N; $A_3$ is N; and $A_4$ is $CR^6$, $X^1$ is $-(CR^{1a}R^{1b})_n G^1-$, n can be 1, 2, or 3; and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $G^1$, $R^3$, $R^6$, $R_A$, $R_B$, $R_E$, $R^7$, Z, $R^g$ and $R^h$ are as described in claim 1.

The present invention also includes compounds in which Y is O, $A_1$ is $CR^3$; $A_2$ is N; $A_3$ is N; and $A_4$ is $CR^6$, $X^1$ is $-(CR^{1a}R^{1b})_p-G-C(R^{1a}R^{1b})-$; and p can be 1 or 2. The present invention also includes compounds in which Y is O, $A_1$ is $CR^3$; $A_2$ is N; $A_3$ is N; and $A_4$ is $CR^6$, $X^1$ is $-(CR^{1a}R^{1b})_p-G^1-C(R^{1a}R^{1b})-$; p is 1 or 2; and $X^2$ is $-N(H)C(O)N(H)-Z$. Compounds included in the present invention are also those in which Y is O, $A_1$ is $CR^3$; $A_2$ is N; $A_3$ is N; and $A_4$ is $CR^6$, $X^1$ is $-(CR^{1a}R^{1b})_p-G^1-C(R^{1a}R^{1b})-$; p is 1 or 2; and $X^2$ is $(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $G^1$, $R^3$, $R^6$, $R_A$, $R_B$, $R_E$, $R^7$, Z, $R^g$ and $R^h$ are as described in claim 1.

The invention includes compounds in which Y is O, $A_1$ is $CR^3$; $A_2$ is N; $A_3$ is $CR^5$; and $A_4$ is N, $X^1$ is $-(CR^{1a}R^{1b})_m-$, and m can be 1, 2, 3, or 4. The invention includes compounds in which Y is O, $A_1$ is $CR^3$; $A_2$ is N; $A_3$ is $CR^5$; and $A_4$ is N, $X^1$ is $-(CR^{1a}R^{1b})_m-$, m can be 1, 2, 3, or 4, and $X^2$ is $-N(H)C(O)N(H)-Z$. Compounds of the invention are also those in which Y is O, $A_1$ is $CR^3$; $A_2$ is N; $A_3$ is $CR^5$; and $A_4$ is N, $X^1$ is $-(CR^{1a}R^{1b})_m-$, m can be 1, 2, 3, or 4, and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $R^3$, $R^5$, $R_A$, $R_B$, $R_E$, $R^7$, Z, $R^g$ and $R^h$ are as described in claim 1

The present invention also includes compounds in which Y is O, $A_1$ is $CR^3$; $A_2$ is N; $A_3$ is $CR^5$; and $A_4$ is N, $X^1$ is $-(CR^{1a}R^{1b})_n G^1-$, and n can be 1, 2, or 3. The present invention also includes compounds in which Y is O, $A_1$ is $CR^3$; $A_2$ is N; $A_3$ is $CR^5$; and $A_4$ is N, $X^1$ is $-(CR^{1a}R^{1b})_n G^1-$, n can be 1, 2, or 3; and $X^2$ is $-N(H)C(O)N(H)-Z$. Compounds included in the present invention are also those in which Y is O, $A_1$ is $CR^2$; $A_2$ is N; $A_3$ is $CR^5$; and $A_4$ is N, $X^1$ is $-(CR^{1a}R^{1b})_n G^1-$, n can be 1, 2, or 3; and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $G^1$, $R^3$, $R^5$, $R_A$, $R_B$, $R_E$, $R^7$, Z, $R^g$ and $R^h$ are as described in claim 1.

The present invention also includes compounds in which Y is O, $A_1$ is $CR^3$; $A_2$ is N; $A_3$ is $CR^5$; and $A_4$ is N, $X^1$ is $-(CR^{1a}R^{1b})_p-G^1-C(R^{1a}R^{1b})-$; and p can be 1 or 2. The present invention also includes compounds in which Y is O, $A_1$ is $CR^3$; $A_2$ is N; $A_3$ is $CR^5$; $A_4$ is N, $X^1$ is $-(CR^{1a}R^{1b})_p-G^1-C(R^{1a}R^{1b})-$; p is 1 or 2; and $X^2$ is $-N(H)C(O)N(H)-Z$. Compounds included in the present invention are also those in which Y is O, $A_1$ is $CR^3$; $A_2$ is N; $A_3$ is $CR^5$; $A_4$ is N, $X^1$ is $-(CR^{1a}R^{1b})_p-G^1-C(R^{1a}R^{1b})-$; p is 1 or 2; and $X^2$ is $-(CR^g R^h)_q-N(H)C(O)N(H)-Z$. It is contemplated that for all the foregoing compounds $R^{1a}$, $R^{1b}$, $R^{2a}$, $R^{2b}$, $R^x$, $R^y$, $G^1$, $R^3$, $R^5$, $R_A$, $R_B$, $R_E$, $R^7$, Z, $R^g$ and $R^h$ are as described in claim 1.

The invention includes compounds in which Y is O, $A_1$ is $CR^3$; $A_2$ is $CR^4$; $A_3$ is N; and $A_4$ is N, $X^1$ is $-(CR^{1a}R^{1b})_m-$, and m can be 1, 2, 3, or 4. The invention includes compounds in which Y is O, $A_1$ is $CR^3$; $A_2$ is $CR^4$; $A_3$ is N; and $A_4$ is N, $X^1$ is —$(CR^{1a}R^{1b})_m$—, m can be 1, 2, 3, or 4, and $X^2$ is —N(H)C(O)N(H)—Z. Compounds of the invention are also those in which Y is O, $A_1$ is $CR^3$; $A_2$ is $CR^4$; $A_3$ is N; and $A_4$ is N, $X^1$ is —$(CR^{1a}R^{1b})_m$—, m can be 1, 2, 3, or 4, and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $R^3$, $R^4$, $R_A$, $R_B$, $R_E$, $R^7$, Z, $R^g$ and $R^h$ are as described in claim 1.

The present invention also includes compounds in which Y is O, $A_1$ is $CR^3$; $A_2$ is $CR^4$; $A_3$ is N; and $A_4$ is N, $X^1$ is —$(CR^{1a}R^{1b})_n G^1$-, and n can be 1, 2, or 3. The present invention also includes compounds in which Y is O, $A_1$ is $CR^3$; $A_2$ is N; $A_3$ is $CR^5$; and $A_4$ is N, $X^1$ is —$(CR^{1a}R^{1b})_n G^1$-, n can be 1, 2, or 3; and $X^2$ is —N(H)C(O)N(H)—Z. Compounds included in the present invention are also those in which Y is O, $A_1$ is $CR^3$; $A_2$ is $CR^4$; $A_3$ is N; and $A_4$ is N, $X^1$ is —$(CR^{1a}R^{1b})_n G^1$-, n can be 1, 2, or 3; and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^4$, $R^3$, $R_A$, $R_B$, $R_E$, $R^7$, Z, $R^g$ and $R^h$ are as described in claim 1.

The present invention also includes compounds in which Y is O, $A_1$ is $CR^3$; $A_2$ is $CR^4$; $A_3$ is N; and $A_4$ is N, $X^1$ is —$(CR^{1a}R^{1b})_p$-$G^1$-$C(R^{1a}R^{1b})$—; and p can be 1 or 2. The present invention also includes compounds in which Y is O, $A_1$ is $CR^3$; $A_2$ is $CR^4$; $A_3$ is N; $A_4$ is N, $X^1$ is —$(CR^{1a}R^{1b})_p$-$G^1$-$C(R^{1a}R^{1b})$—; p is 1 or 2; and $X^2$ is —N(H)C(O)N(H)—Z. Compounds included in the present invention are also those in which Y is O, $A_1$ is N; $A_2$ is $CR^4$; $A_3$ is $CR^5$; $A_4$ is N, $X^1$ is —$(CR^{1a}R^{1b})_p$-$G^1$-$C(R^{1a}R^{1b})$; p is 1 or 2; and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^4$, $R^3$, $R_A$, $R_B$, $R_E$, $R^7$, Z, $R^g$ and $R^h$ are as described in claim 1.

The present invention also includes compounds in which Y is O, $A_1$ is N; $A_2$ is $CR^4$; $A_3$ is $CR^5$; and $A_4$ is $CR^6$, $X^1$ is —$(CR^{1a}R^{1b})_m$—, and m can be 1, 2, 3, or 4. The invention includes compounds in which Y is O, $A_1$ is N; $A_2$ is $CR^4$; $A_3$ is $CR^5$; and $A_4$ is $CR^6$, $X^1$ is —$(CR^{1a}R^{1b})_m$—, m can be 1, 2, 3, or 4, and $X^2$ is —N(H)C(O)N(H)—Z. Compounds of the invention are also those in which Y is O, $A_1$ is N; $A_2$ is $CR^4$; $A_3$ is $CR^5$; and $A_4$ is $CR^6$, $X^1$ is —$(CR^{1a}R^{1b})_m$—, m can be 1, 2, 3, or 4, and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $R^4$, $R^5$, $R^6$, $R_A$, $R_B$, $R_E$, $R^7$, Z, $R^g$ and $R^h$ are as described in claim 1

The present invention also includes compounds in which Y is O, $A_1$ is N; $A_2$ is $CR^4$; $A_3$ is $CR^5$; and $A_4$ is $CR^6$, $X^1$ is —$(CR^{1a}R^{1b})_n G^1$-, and n can be 1, 2, or 3. The present invention also includes compounds in which Y is O, $A_1$ is N; $A_2$ is $CR^4$; $A_3$ is $CR^5$; and $A_4$ is $CR^6$, $X^1$ is —$(CR^{1a}R^{1b})_n G^1$-, n can be 1, 2, or 3; and $X^2$ is —N(H)C(O)N(H)—Z. Compounds included in the present invention are also those in which Y is O, $A_1$ is N; $A_2$ is $CR^4$; $A_3$ is $CR^5$; and $A_4$ is $CR^6$, $X^1$ is —$(CR^{1a}R^{1b})_n G^1$-, n can be 1, 2, or 3; and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^4$, $R^5$, $R^6$, $R_A$, $R_B$, $R_E$, $R^7$, Z, $R^g$ and $R^h$ are as described in claim 1.

The present invention also includes compounds in which Y is O, $A_1$ is N; $A_2$ is $CR^4$; $A_3$ is $CR^5$; and $A_4$ is $CR^6$, $X^1$ is —$(CR^{1a}R^{1b})_p$-G1-$C(R^{1a}R^{1b})$—; and p can be 1 or 2. The present invention also includes compounds in which Y is O, $A_1$ is N; $A_2$ is $CR^4$; $A_3$ is $CR^5$; $A_4$ is $CR^6$, $X^1$ is —$(CR^{1a}R^{1b})_p$-$G^1$-$C(R^{1a}R^{1b})$—; p is 1 or 2; and $X^2$ is —N(H)C(O)N(H)—Z. Compounds included in the present invention are also those in which Y is O, $A_1$ is N; $A_2$ is $CR^4$; $A_3$ is $CR^5$; $A_4$ is $CR^6$, $X^1$ is —$(CR^{1a}R^{1b})_p$-$G^1$-$C(R^{1a}R^{1b})$—; p is 1 or 2; and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^4$, $R^5$, $R^6$, $R_A$, $R_B$, $R_E$, $R^7$, Z, $R^g$ and $R^h$ are as described in claim 1.

The invention includes compounds in which Y is O, $A_1$ is $CR^3$; $A_2$ is N; $A_3$ is $CR^5$; and $A_4$ is $CR^6$, $X^1$ is —$(CR^{1a}R^{1b})_m$—, and m can be 1, 2, 3, or 4. The invention includes compounds in which Y is O, $A_1$ is $CR^3$; $A_2$ is N; $A_3$ is $CR^5$; and $A_4$ is $CR^6$, $X^1$ is —$(CR^{1a}R^{1b})_m$—, m can be 1, 2, 3, or 4, and $X^2$ is —N(H)C(O)N(H)—Z. Compounds of the invention are also those in which Y is O, $A_1$ is $CR^3$; $A_2$ is N; $A_3$ is $CR^5$; and $A_4$ is $CR^6$, $X^1$ is —$(CR^{1a}R^{1b})_m$—, m can be 1, 2, 3, or 4, and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $R^3$, $R^5$, $R^6$, $R_A$, $R_B$, $R_E$, $R^7$, Z, $R^g$ and $R^h$ are as described in claim 1

The present invention also includes compounds in which Y is O, $A_1$ is $CR^3$; $A_2$ is N; $A_3$ is $CR^5$; and $A_4$ is $CR^6$, $X^1$ is —$(CR^{1a}R^{1b})_n G^1$-, and n can be 1, 2, or 3. The present invention also includes compounds in which Y is O, $A_1$ is $CR^3$; $A_2$ is N; $A_3$ is $CR^5$; and $A_4$ is $CR^6$, $X^1$ is —$(CR^{1a}R^{1b})_n G^1$-, n can be 1, 2, or 3; and $X^2$ is —N(H)C(O)N(H)—Z Compounds included in the present invention are also those in which Y is O, $A_1$ is $CR^3$; $A_2$ is N; $A_3$ is $CR^5$; and $A_4$ is $CR^6$, $X^1$ is —$(CR^{1a}R^{1b})_n G^1$-, n can be 1, 2, or 3; and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^3$, $R^5$, $R^6$, $R_A$, $R_B$, $R_E$, $R^7$, Z, $R^g$ and $R^h$ are as described in claim 1.

The present invention also includes compounds in which Y is O, $A_1$ is $CR^3$; $A_2$ is N; $A_3$ is $CR^5$; and $A_4$ is $CR^6$, $X^1$ is —$(CR^{1a}R^{1b})_p$-$G^1$-$C(R^{1a}R^{1b})$—; and p can be 1 or 2. The present invention also includes compounds in which Y is O, $A_1$ is $CR^3$; $A_2$ is N; $A_3$ is $CR^5$; $A_4$ is $CR^6$, $X^1$ is —$(CR^{1a}R^{1b})_p$-$G^1$-$C(R^{1a}R^{1b})$—; p is 1 or 2; and $X^2$ is —N(H)C(O)N(H)—Z. Compounds included in the present invention are also those in which Y is O, $A_1$ is $CR^3$; $A_2$ is N; $A_3$ is $CR^5$; $A_4$ is $CR^6$, $X^1$ is —$(CR^{1a}R^{1b})_p$-$G^1$-$C(R^{1a}R^{1b})$—; p is 1 or 2; and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^3$, $R^5$, $R^6$, $R_A$, $R_B$, $R_E$, $R^7$, Z, $R^g$ and $R^h$ are as described in claim 1.

The invention includes compounds in which Y is O, $A_1$ is $CR^3$; $A_2$ is $CR^4$; $A_3$ is N; and $A_4$ is $CR^6$, $X^1$ is —$(CR^{1a}R^{1b})_m$—, and m can be 1, 2, 3, or 4. The invention includes compounds in which Y is O, $A_1$ is $CR^3$; $A_2$ is $CR^4$; $A_3$ is N; and $A_4$ is $CR^6$, $X^1$ is —$(CR^{1a}R^{1b})_m$—, m can be 1, 2, 3, or 4, and $X^2$ is —N(H)C(O)N(H)—Z. Compounds of the invention are also those in which Y is O, $A_1$ is $CR^3$; $A_2$ is $CR^4$; $A_3$ is N; and $A_4$ is $CR^6$, $X^1$ is —$(CR^{1a}R^{1b})_m$—, m can be 1, 2, 3, or 4, and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $R^3$, $R^4$, $R^6$, $R_A$, $R_B$, $R_E$, $R^7$, Z, $R^g$ and $R^h$ are as described in claim 1

The present invention also includes compounds in which Y is O, $A_1$ is $CR^3$; $A_2$ is $CR^4$; $A_3$ is N; and $A_4$ is $CR^6$, $X^1$ is —$(CR^{1a}R^{1b})_n G^1$-, and n can be 1, 2, or 3. The present invention also includes compounds in which Y is O, $A_1$ is $CR^3$; $A_2$ is $CR^4$; $A_3$ is N; and $A_4$ is $CR^6$, $X^1$ is —$(CR^{1a}R^{1b})_n G^1$-, n can be 1, 2, or 3; and $X^2$ is —N(H)C(O)N(H)—Z. Compounds included in the present invention are also those in which Y is O, $A_1$ is $CR^3$; $A_2$ is $CR^4$; $A_3$ is N; and $A_4$ is $CR^6$, $X^1$ is —$(CR^{1a}R^{1b})_n G^1$-, n can be 1, 2, or 3; and $X^2$ is —$(CR^g R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^3$, $R^4$, $R^6$, $R_A$, $R_B$, $R_E$, $R^7$, Z, $R^g$ and $R^h$ are as described in claim 1.

The present invention also includes compounds in which Y is O, $A_1$ is $CR^3$; $A_2$ is $CR^4$; $A_3$ is N; and $A_4$ is $CR^6$, $X^1$ is —$(CR^{1a}R^{1b})_p$-$G^1$-$C(R^{1a}R^{1b})$—; and p can be 1 or 2. The present invention also includes compounds in which Y is O, $A_1$ is $CR^3$; $A_2$ is $CR^4$; $A_3$ is N; $A_4$ is $CR^6$, $X^1$ is —$(CR^{1a}R^{1b})_p$-$G^1$-$C(R^{1a}R^{1b})$—; p is 1 or 2; and $X^2$ is —N(H)C(O)N(H)—Z. Compounds included in the present invention are also those in which Y is O, $A_1$ is $CR^3$; $A_2$ is $CR^4$; $A_3$ is N; $A_4$ is $CR^6$, $X^1$ is —$(CR^{1a}R^{1b})_p$-$G^1$-$C(R^{1a}R^{1b})$—; p is 1 or 2; and $X^2$ is $(CR^gR^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^3$, $R^4$, $R^6$, $R_A$, $R_B$, $R_E$, $R^7$, Z, $R^g$ and $R^h$ are as described in claim 1.

The invention includes compounds in which Y is O, $A_1$ is $CR^3$; $A_2$ is $CR^4$; $A_3$ is $CR^5$; and $A_4$ is N, $X^1$ is —$(CR^{1a}R^{1b})_m$—, and m can be 1, 2, 3, or 4. The invention includes compounds in which Y is O, $A_1$ is $CR^3$; $A_2$ is $CR^4$; $A_3$ is $CR^5$; and $A_4$ is N, $X^1$ is —$(CR^{1a}R^{1b})_m$—, m can be 1, 2, 3, or 4, and $X^2$ is —N(H)C(O)N(H)—Z. Compounds of the invention are also those in which Y is O, $A_1$ is $CR^3$; $A_2$ is $CR^4$; $A_3$ is $CR^5$; and $A_4$ is N, $X^1$ is —$(CR^{1a}R^{1b})_m$—, m can be 1, 2, 3, or 4, and $X^2$ is —$(CR^gR^h)_q$—N(H)C(O)N(H)—Z. It is contemplated that for all the foregoing compounds $R^{1a}$, $R^{1b}$, $R^{2a}$, $R^{2b}$, $R^x$, $R^y$, $R^3$, $R^4$, $R^5$, $R_A$, $R_B$, $R_E$, $R^7$, Z, $R^g$ and $R^h$ are as described in claim 1

The present invention also includes compounds in which Y is O, $A_1$ is $CR^3$; $A_2$ is $CR^4$; $A_3$ is $CR^5$; and $A_4$ is N, $X^1$ is —$(CR^{1a}R^{1b})_n G^1$-, and n can be 1, 2, or 3. The present invention also includes compounds in which Y is O, $A_1$ is $CR^3$; $A_2$ is $CR^4$; $A_3$ is $CR^5$; and $A_4$ is N, $X^1$ is —$(CR^{1a}R^{1b})_n G$-, n can be 1, 2, or 3; and $X^2$ is —N(H)C(O)N(H)—Z. Compounds included in the present invention are also those in which Y is O, $A_1$ is $CR^3$; $A_2$ is $CR^4$; $A_3$ is $CR^5$; and $A_4$ is N, $X^1$ is —$(CR^{1a}R^{1b})_n G^1$-, n can be 1, 2, or 3; and $X^2$ is —$(CR^gR^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^3$, $R^4$, $R^5$, $R_A$, $R_B$, $R_E$, $R^7$, Z, $R^g$ and $R^h$ are as described in claim 1.

The present invention also includes compounds in which Y is O, $A_1$ is $CR^3$; $A_2$ is $CR^4$; $A_3$ is $CR^5$; and $A_4$ is N, $X^1$ is —$(CR^{1a}R^{1b})_p$-$G^1$-$C(R^{1a}R^{1b})$—; and p can be 1 or 2. The present invention also includes compounds in which Y is O, $A_1$ is $CR^3$; $A_2$ is $CR^4$; $A_3$ is $CR^5$; $A_4$ is N, $X^1$ is —$(CR^{1a}R^{1b})_p$-$G^1$-$C(R^{1a}R^{1b})$—; p is 1 or 2; and $X^2$ is —N(H)C(O)N(H)—Z Compounds included in the present invention are also those in which Y is O, $A_1$ is $CR^3$; $A_2$ is $CR^4$; $A_3$ is $CR^5$; $A_4$ is N, $X^1$ is —$(CR^{1a}R^{1b})_p$-$G^1$-$C(R^{1a}R^{1b})$—; p is 1 or 2; and $X^2$ is —$(CR^gR^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^3$, $R^4$, $R^5$, $R_A$, $R_B$, $R_E$, $R^7$, Z, $R^g$ and $R^h$ are as described in claim 1.

The invention includes compounds in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, and m can be 1, 2, 3, or 4. The invention includes compounds in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, m is 1, and $X^2$ is —N(H)C(O)N(H)—Z. Compounds included in the present invention are those in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, m is 1, $X^2$ is —N(H)C(O)N(H)—Z, and Z is a monocyclic or bicyclic ring selected from the group consisting of cycloalkyl, cycloalkenyl, heterocycle, heteroaryl and aryl; wherein each Z is independently unsubstituted or substituted with 1, 2, 3 or 4 substituents selected from the group consisting of oxo, alkyl, haloalkyl, halogen, —$NO_2$, —CN, —OH, alkoxy, haloalkoxy, —$NH_2$, —N(H)(alkyl), —N(alkyl)$_2$, —C(O)alkyl, —C(O)OH, —C(O)Oalkyl, —C(O)N$H_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl), —S(O)$_2$N(alkyl)$_2$, $R_E$, and —$C(R^{1a}R^{1b})_q$—$R_E$. Preferably Z is a bicyclic ring, most preferably heteroaryl, most preferably indazolyl.

zolyl. Compounds of the invention are also those in which Y is O, $A_1$ is $CR^3$; $A_2$ is $CR^4$; $A_3$ is $CR^5$; and $A_4$ is $CR^6$, $X^1$ is —$C(R^{1a}R^{1b})_m$—, m is 1, and $X^2$ is —$(CR^gR^h)_q$—N(H)C(O)N(H)—Z. It is contemplated that for all the foregoing compounds $R^{1a}$, $R^{1b}$, $R^{2a}$, $R^{2b}$, $R^x$, $R^y$, $R^3$, $R^4$, $R^5R^6$, $R_A$, $R_B$, $R_E$, $R^7$, Z, $R^g$ and $R^h$ are as described in claim 1.

The invention includes compounds in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, m is 2, and $X^2$ is —N(H)C(O)N(H)—Z. Compounds included in the present invention are those in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, m is 2, $X^2$ is —N(H)C(O)N(H)—Z, and Z is a monocyclic or bicyclic ring selected from the group consisting of cycloalkyl, cycloalkenyl, heterocycle, heteroaryl and aryl; wherein each Z is independently unsubstituted or substituted with 1, 2, 3 or 4 substituents selected from the group consisting of oxo, alkyl, haloalkyl, halogen, —$NO_2$, —CN, —OH, alkoxy, haloalkoxy, —$NH_2$, —N(H)(alkyl), —N(alkyl)$_2$, —C(O)alkyl, —C(O)OH, —C(O)Oalkyl, —C(O)N$H_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl), —S(O)$_2$N(alkyl)$_2$, $R_E$, and —$(CR^{1a}R^{1b})_q$—$R_E$. Preferably Z is a bicyclic ring, most preferably heteroaryl, most preferably indazolyl. Compounds of the invention are also those in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, m is 2, and $X^2$ is —$(CR^gR^h)_q$—N(H)C(O)N(H)—Z. It is contemplated that for all the foregoing compounds $R^{1a}$, $R^{1b}$, $R^{2a}$, $R^{2b}$, $R^x$, $R^y$, $R^3$, $R^4$, $R^5R^6$, $R_A$, $R_B$, $R_E$, $R^7$, Z, $R^g$ and $R^h$ are as described in claim 1

The invention includes compounds in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, m is 3, and $X^2$ is —N(H)C(O)N(H)—Z. Compounds included in the present invention are those in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, m is 3, $X^2$ is —N(H)C(O)N(H)—Z, and Z is a monocyclic or bicyclic ring selected from the group consisting of cycloalkyl, cycloalkenyl, heterocycle, heteroaryl and aryl; wherein each Z is independently unsubstituted or substituted with 1, 2, 3 or 4 substituents selected from the group consisting of oxo, alkyl, haloalkyl, halogen, —$NO_2$, —CN, —OH, alkoxy, haloalkoxy, —$NH_2$, —N(H)(alkyl), —N(alkyl)$_2$, —C(O)alkyl, —C(O)OH, —C(O)Oalkyl, —C(O)N$H_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl), —S(O)$_2$N(alkyl)$_2$, $R_E$, and —$(CR^{1a}R^{1b})_q$—$R_E$. Preferably Z is a bicyclic ring, most preferably heteroaryl, most preferably indazolyl. Compounds of the invention are also those in which Y is O, $A_1$ is $CR^3$; $A_2$ is $CR^4$; $A_3$ is $CR^5$; and $A_4$ is $CR^6$, $X^1$ is —$(CR^{1a}R^{1b})_m$—, m is 3, and $X^2$ is —$(CR^gR^h)_q$—N(H)C(O)N(H)—Z. It is contemplated that for all the foregoing compounds $R^{1a}$, $R^{1b}$, $R^{2a}$, $R^x$, $R^y$, $R^3$, $R^4$, $R^5R^6$, $R_A$, $R_B$, $R_E$, $R^7$, Z, $R^g$ and $R^h$ are as described in claim 1

The present invention also includes compounds in which Y is O, $A_1$ is $CR^3$; $A_2$ is $CR^4$; $A_3$ is $CR^5$; and $A_4$ is $CR^6$, $X^1$ is —$(CR^{1a}R^{1b})_n G^1$-, and n can be 1, 2, or 3. The present invention also includes compounds in which Y is O, $A_1$ is $CR^3$; $A_2$ is $CR^4$; $A_3$ is $CR^5$; and $A_4$ is $CR^6$, $X^1$ is —$(CR^{1a}R^{1b})_n G^1$-, n is 2, G is O; and $X^2$ is —N(H)C(O)N(H)—Z The present invention also includes compounds in which Y is O, $A_1$ is $CR^3$; $A_2$ is $CR^4$; $A_3$ is $CR^5$; and $A_4$ is $CR^6$, $X^1$ is —$(CR^{1a}R^{1b})_n G^1$-, n is 2, G is N($R^x$); $R^x$ is hydrogen, alkyl, haloalkyl, $R^y$, —C(O)Oalkyl, or —C(O)O$R^y$; and $X^2$ is —N(H)C(O)N(H)—Z. Compounds included in the present invention are also those in which Y is O, $A_1$ is $CR^3$; $A_2$ is $CR^4$; $A_3$ is $CR^5$; and $A_4$ is $CR^6$, $X^1$ is —$(CR^{1a}R^{1b})_n G^1$-, n can be 1, 2, or 3; and $X^2$ is —$(CR^g$ $R^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^3$, $R^4$, $R^5R^6$, $R_A$, $R_B$, $R_E$, $R^7$, Z, $R^g$ and $R^h$ are as described in claim 1.

The present invention also includes compounds in which Y is O, $A_1$ is $CR^3$; $A_2$ is $CR^4$; $A_3$ is N; and $A_4$ is $CR^6$, $X^1$ is —$(CR^{1a}R^{1b})_p$-$G^1$-$C(R^{1a}R^{1b})$—; and p can be 1 or 2. The present invention also includes compounds in which Y is O, $A_1$ is $CR^3$; $A_2$ is $CR^4$; $A_3$ is N; and $A_4$ is $CR^6$, $X^1$ is —$(CR^{1a}R^{1b})_p$-$G^1$-$C(R^{1a}R^{1b})$—; p is 1 or 2; and $X^2$ is —N(H)C(O)N(H)—Z. Compounds included in the present invention are also those in which Y is O, $A_1$ is $CR^3$; $A_2$ is $CR^4$; $A_3$ is $CR^5$; and $A_4$ is $CR^6$, $X^1$ is —$(CR^{1a}R^{1b})_p$-$G^1$-$C(R^{1a}R^{1b})$—; p is 1 or 2; and $X^2$ is —$(CR^gR^h)_q$—N(H)C(O)N(H)—Z. It is contemplated that for all the foregoing compounds $R^{1a}$, $R^{1b}$, $R^{2a}$, $R^{2b}$, $R^x$, $R^y$, $G^1$, $R^3$, $R^4$, $R^5$ $R^6$, $R_A$, $R_B$, $R_E$, $R^7$, Z, $R^g$ and $R^h$ are as described in claim 1.

Compositions of the Invention

The invention provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention. The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Methods of the Invention

Compounds and compositions of the invention are useful for ameliorating or preventing disorders involving VR1 receptor activation such as, but not limited to, pain, inflammatory thermal hyperalgesia, bladder overactivity, and urinary incontinence as described by Nolano, M. et al., *Pain, Vol.* 81, pages 135-145, (1999); Caterina, M. J. and Julius, D., *Annu. Rev. Neurosci. Vol.* 24, pages 487-517 (2001); Caterina, M. J. et al., *Science Vol.* 288 pages 306-313 (2000); Caterina, M. J. et al., *Nature Vol.* 389 pages 816-824 (1997); Fowler, C. *Urology Vol.* 55 pages 60-64 (2000); and Davis, J. et al., *Nature Vol.* 405 pages 183-187.

The present invention also provides pharmaceutical compositions that comprise compounds of the present invention. The pharmaceutical compositions comprise compounds of the present invention that may be formulated together with one or more non-toxic pharmaceutically acceptable carriers and diluents.

EXAMPLES

The following Examples are intended as an illustration of and not a limitation upon the scope of the invention as defined in the appended claims.

Example 1

1-(1H-indazol-4-yl)-3-(spiro[chroman-2,1'-cyclohexane]-4-yl)urea

Example 1A spiro[chroman-2,1'-cyclohexan]-4-one

A mixture of 2'-hydroxyacetophenone (Aldrich, CAS#118-93-4, 2.72 g, 20 mmol), cyclohexanone (2.7 mL, 26.1 mmol), and pyrrolidine (1.66 mL, 19.9 mmol) was stirred in 6 mL toluene at room temperature for 1 h and at reflux (Dean-Stark trap) for 4 h. After cooling to room temperature, the mixture was diluted with ether (30 mL), washed sequentially with 2N HCl (10 mL), 2N NaOH (10 mL), and $H_2O$ (10 mL), dried over $Na_2SO_4$, and filtered. Evaporation of volatiles in vacuo afforded the crude title compound, which was used without further purification.

Example 1B spiro[chroman-2,1'-cyclohexan]-4-amine

To a solution of the product from Example 1A (3.022 g, 13.99 mmol) in methanol (50 mL) was added methoxylamine hydrochloride (1.17 g, 14.0 mmol) and pyridine (5.7 mL, 70.5 mmol). The mixture was stirred overnight at room temperature and was then evaporated in vacuo. The residue was partitioned between ethyl acetate and $H_2O$, and the organic layer was dried over $Na_2SO_4$, filtered and evaporated in vacuo. The residue thus obtained was dissolved in methanol (50 mL) and was hydrogenated (balloon) over 10% Pd-on-carbon in the presence of 4 drops of conc. HCl overnight at room temperature. After this time, the catalyst was filtered off (Celite), and the filtrate was evaporated in vacuo. The residue was taken up in ether (50 mL) and was extracted with 1N HCl (3×20 mL). These acidic extracts were then basified to pH 10 with 2N NaOH and were extracted with ethyl acetate (3×20 mL). The organic extracts were dried over $Na_2SO_4$, filtered and evaporated in vacuo to yield the title compound as a yellow oil, 880 mg (29%). $^1$H NMR (300 MHz, DMSO-$d_6$) δ ppm 7.52 (m, 1H), 7.06 (m, 1H), 6.82 (td; J=7.4, 1.3 Hz; 1H), 6.69 (dd; J=8.1, 1.3 Hz; 1H), 3.83 (dd; J=11.1, 6.3 Hz; 1H), 2.08 (dd; J=13.5, 6.3 Hz; 1H), 1.90 (m, 1H), 1.74 (m, 2H), 1.31-1.57 (m, 8H); MS (ESI) m/z 218 (M+H).

Example 1C methyl 4-(3-spiro[chroman-2,1'-cyclohexan]-4-ylureido)-1H-indazole-1-carboxylate The product from Example 1B (880 mg, 4.06 mmol) was stirred with the product from Example 1H (1.34 g, 4.04 mmol) and diisopropylethyl amine (1.1 mL, 6.33 mmol) in 20 mL N,N-dimethyl formamide at room temperature for 2 h. After this time, most of the N,N-dimethyl formamide was removed in vacuo, and the residue was diluted with $H_2O$. The precipitate thus formed was collected by filtration and was air-dried to afford the title compound as a tan solid, which was used without further purification.

Example 1D 1-(1H-indazol-4-yl)-3-(spiro[chroman-2,1'-cyclohexane]-4-yl)urea

The product from Example 1C (4.06 mmol) was suspended in methanol (20 mL) and was treated with 5N methanolic NaOH (3.3 mL, 16.5 mmol). The mixture was stirred at room temperature for 45 min, then it was poured into $H_2O$ (100 mL). The precipitate that formed was collected by filtration and was air-dried to afford the title compound as an off-white solid, 794 mg (43%). $^1$H NMR (300 MHz, DMSO-$d_6$) δ ppm 13.01 (br, 1H), 8.67 (s, 1H), 8.06 (s, 1H), 7.69 (d, J=7.5 Hz, 1H), 7.31 (d, J=7.8 Hz, 1H), 7.23 (J=7.8 Hz, 1H), 7.16 (m, 1H), 7.08 (d, J=8.5 Hz, 1H), 6.90 (td; J=7.5, 1.0 Hz; 1H), 6.80 (dd; J=7.9, 1.0 Hz; 1H), 6.72 (d, J=8.1 Hz, 1H), 4.98 (m, 1H), 2.24 (m, 1H), 1.33-1.82 (m, 11H). MS (ESI$^+$) m/z 377 (M+H).

Example 1E

4-nitro-1H-indazole

2-Methyl-3-nitroaniline (20 g) in acetic acid (~200 mL) was treated with $NaNO_2$ (20 g) in water (50 mL) at 4° C. (mechanical stirring). The reaction mixture was allowed to warm to room temperature and stir overnight. The solvent was removed under reduced pressure. The residue was treated with water (700 mL) and the mixture was filtered. The solid was dried at 45° C. in a vacuum oven overnight to provide the title compound. $^1$H NMR (DMSO-$d_6$) δ 8.56 (s, 1H), 8.2-8.05 (dd, 2H), 7.6 (t, 1H).

Alternatively, to a 4-necked 5-L jacketed round bottom flask fitted with a mechanical stirrer and a thermocouple was charged the nitroaniline (100 g, 1.0 equiv.) and acetic acid (2000 mL). The solution was cooled to 14° C. A chilled to about 1° C. (ice-water bath) solution of sodium nitrite (100 g, 2.2 equiv.) in water (250 mL) was added quickly in one portion. The internal temperature rose from 14° C. to 27.6° C. over 5 min., stayed at this temperature for 5 min. before gradually cooling to 15° C. The mixture was stirred for 24 h after which it was concentrated in vacuo to an approximate volume of 500 mL. The residue was re-slurried in water (1800 mL) at ambient temperature for 21 hours. The orange solid was filtered, washed with water (3×250 mL), and dried in a vacuum oven at 70° C. to afford 97.0 g of the title compound as a bright orange solid.

Example 1F methyl 4-nitro-1H-indazole-1-carboxylate

NaH (0.3 g, 12.5 mmol) in N,N-dimethylformamide (5 mL) was treated with the product of Example 1E (1.33 g, 10 mmol) at 0° C. The reaction mixture was allowed to warm to room temperature and stir for 1 hour. The mixture was treated with methyl chloroformate (0.9 mL) and stirred at room temperature for 3 hours. The mixture was treated with water and filtered to provide the title compound as a solid. $^1$H NMR (300 MHz, DMSO-$d_6$) δ 4.1 9 (s, 3H), 7.9 (t, 1H), 8.38 (d, 1H), 8.62 (d, 1H), 8.85 (s, 1H).

Alternatively, to a 3-necked 2-L jacketed flask fitted with a mechanical stirrer, a thermocouple, and an addition funnel was charged 95.2 g of the product of Example 1E and N,N-dimethylformamide (650 mL). The dark solution was cooled to 10° C. and 1,8-diazabicyclo[5.4.0]undec-7-ene (96.0 g, 1.1 equiv.) was added via addition funnel so that the internal temperature did not go beyond 15° C. After cooling the mixture back to 10° C., methyl chloroformate (108.5 g, 2.0 equiv.) was added via addition funnel so that the internal temperature did not go beyond 25° C. After 1 hour stirring at 10° C., aqueous 10% potassium phosphate diacid in water (500 mL) was added and the mixture was stirred for 15 hours. The resulting brown solid was filtered and the reaction vessel rinsed with aqueous 10% potassium phosphate diacid in water (2×150 mL). The rinses were added to the solid on the filter. The resulting solid was washed with aqueous 10% potassium phosphate diacid in water (2×200 mL), water (2×200 mL), dried in a vacuum oven at 70° C. to afford 122.2 g of a dark brown solid. The solid was reslurried in isopropyl acetate (2000 mL) for 2 hours. The solid was filtered, washed with fresh isopropyl acetate (2×250 mL), and dried in a vacuum oven at 70° C. to afford 110.2 g of the title compound as a light brown solid.

Example 1G methyl 4-amino-1H-indazole-1-carboxylate

The product of Example 1F (1.66 g, 7.5 mmol) and 10% Pd/C were combined in ethanol (20 mL) and exposed to a hydrogen atmosphere. The reaction mixture was heated at 80° C. for 20 minutes, allowed to cool to room temperature, and filtered through Celite. The filtrate was evaporated to provide title compound. $^1$H NMR (300 MHz, DMSO-$d_6$) δ 6.1 (s, 2H), 6.41 (dd, 1H), 7.21 (m, 2H), 8.42 (s, 1H).

Alternatively, to the reaction vessel was charged the product of Example 1F, methanol (2000 mL), and 5% Pd/C (10.6 g). The mixture was pressured with $H_2$ (40 psi) and shaken at ambient temperature. The reaction was completed in 1.5 hours. The mixture was filtered to obtain the product in methanol. Conc., 37% HCl (100 mL) was added to the reaction mixture. The product solution was concentrated to furnish a light brown solid. The solid was reslurried in isopropyl alcohol (200 mL) for 15 minutes. The solid was filtered and washed with fresh isopropyl alcohol (3×50 mL), and dried in a vacuum oven to provide 94.9 g of 4-aminoindazole-1-carboxylic acid methyl ester, HCl salt as a light brown solid.

Example 1H

4-(2,5-dioxo-pyrrolidin-1-yloxycarbonylamino)-indazole-1-carboxylic acid methyl ester The product of Example 1G (1.9 g, 10 mmol) and disuccinimidylcarbonate (2.8 g, 11 mmol) were mixed in acetonitrile (100 mL) for 48 hours under nitrogen atmosphere. The solid was isolated by filtration, washed with acetonitrile (10 mL) and dried under vacuum at ambient temperature to give the title compound (2.56 g, 77%) as off-white solid.

Example 2

1-(7-fluorospiro[chroman-2,1'-cyclohexane]-4-yl)-3-(1H-indazol-4-yl)urea

Example 2A

7-fluorospiro[chroman-2,1'-cyclohexan]-4-one

The title compound was prepared using the procedure as described in Example 1A, substituting 4'-fluoro-2'-hydroxyacetophenone (Aldrich, CAS#1481-27-2) for 2'-hydroxyacetophenone. $^1$H NMR (300 MHz, DMSO-$d_6$) δ ppm 7.78 (dd; J=8.5, 6.8 Hz; 1H), 6.88 (m, 2H), 2.78 (s, 2H), 1.88 (m, 2H), 1.44-1.63 (m, 6H), 1.24-1.37 (m, 2H). MS (DCI$^+$) m/z 235 (M+H), 252 (M+NH$_4$).

Example 2B

7-fluorospiro[chroman-2,1'-cyclohexan]-4-amine

The title compound was prepared using the procedure as described in Example 1B, substituting Example 2A for Example 1A. $^1$H NMR (300 MHz, DMSO-$d_6$) δ ppm 7.57 (m, 1H), 6.52 (m, 2H), 3.82 (m, 1H), 2.11 (m, 1H), 1.92 (m, 1H), 1.38-1.73 (m, 10H). MS (DCI$^+$) 236 (M+H).

Example 2C methyl 4-(3-(7-fluorospiro[chroman-2,1'-cyclohexane]-4-yl)ureido)-1H-indazole-1-carboxylate The title compound was prepared using the procedure as described in Example 1C, substituting Example 2B for Example 1B. The crude compound was then used without further purification.

Example 2D 1-(7-fluorospiro[chroman-2,1'-cyclohexane]-4-yl)-3-(1H-indazol-4-yl)urea The title compound was prepared using the procedure as described in Example 1D, substituting Example 2C for Example 1C. $^1$H NMR (300 MHz, DMSO-$d_6$) δ ppm 13.00 (s, 1H), 8.68 (s, 1H), 8.06 (s, 1H), 7.67 (d, J=7.4 Hz, 1H), 7.35 (m, 1H), 7.22 (t, J=8.0 Hz, 1H), 7.08 (d, J=8.3 Hz, 1H), 6.75 (m, 2H), 6.64 (dd; J=10.3, 2.7 Hz; 1H), 4.96 (m, 1H), 2.25 (dd; J=13.5, 6.5 Hz; 1H), 1.33-1.79 (m, 11H). MS (ESI) m/z 395 (M+H), 417 (M+Na).

Example 3

1-(7-fluorospiro[chroman-2,1'-cyclobutane]-4-yl)-3-(1H-indazol-4-yl)urea

Example 3A 7-fluorospiro[chroman-2,1'-cyclobutan]-4-one

The title compound was prepared using the procedure as described in Example 1A, substituting 4'-fluoro-2'-hydroxyacetophenone (Aldrich, CAS#1481-27-2) for 2'-hydroxyacetophenone and substituting cyclobutanone for cyclohexanone. $^1$H NMR (300 MHz, DMSO-$d_6$) δ ppm 7.80 (dd; J=8.6, 6.6 Hz; 1H), 6.93 (m, 2H), 2.98 (s, 2H), 2.07-2.28 (m, 4H), 1.73-1.86 (m, 2H); MS (DCI$^+$) m/z 207 (M+H), 224 (M+NH$_4$).

Example 3B 7-fluorospiro[chroman-2,1'-cyclobutan]-4-amine

The title compound was prepared using the procedure as described in Example 1B, substituting Example 3A for Example 1A. $^1$H NMR (300 MHz, DMSO-$d_6$) δ ppm 7.52 (m, 1H), 6.67 (m, 1H), 6.52 (dd; J=9.5, 2.7 Hz; 1H), 3.80 (dd; J=10.9, 5.8 Hz; 1H), 2.25 (m, 2H), 2.09 (m, 4H), 1.57-1.71 (m, 2H). MS (DCI$^+$) m/z 208 (M+H), 225 (M+NH$_4$).

Example 3C methyl 4-(3-(7-fluorospiro[chroman-2,1'-cyclobutane]-4-yl)ureido)-1H-indazole-1-carboxylate The title compound was prepared using the procedure as described in Example 1C, substituting Example 3B for Example 1B. The crude compound was then used without further purification.

Example 3D 1-(7-fluorospiro[chroman-2,1'-cyclobutane]-4-yl)-3-(1H-indazol-4-yl)urea The title compound was prepared using the procedure as described in Example 1D, substituting Example 3C for Example 1C. $^1$H NMR (300 MHz, DMSO-$d_6$) δ ppm 13.01 (br, 1H), 8.71 (s, 1H), 8.07 (s, 1H), 7.68 (d, J=7.4 Hz, 1H), 7.25 (m, 2H), 7.09 (d, J=8.2 Hz, 1H), 6.78 (m, 2H), 6.67 (dd; J=10.5, 2.7 Hz; 1H), 4.94 (m, 1H), 2.41 (dd; J=13.4, 5.5 Hz; 1H), 2.21 (m, 3H), 1.70-1.97 (m, 4H). MS (ESI$^+$) m/z 367 (M+H).

Example 4

1-(7-fluorospiro[chroman-2,1'-cyclobutane]-4-yl)-3-(1-methyl-1H-indazol-4-yl)urea A solution of Example 3D (483 mg, 1.32 mmol) in N,N-dimethylformamide (5 mL) was treated with 60% NaH (65 mg, 1.63 mmol), and the mixture was stirred at room temperature for 45 min. Dimethyl sulfate (0.14 mL, 1.48 mmol) was then added, and the reaction was allowed to stir for 1 h. Concentration in vacuo, followed by silica gel chromatography (98:2 CH$_2$Cl$_2$-methanol, eluent), afforded the title compound as an off-white solid, 121 mg (24%). $^1$H NMR (300 MHz, DMSO-$d_6$) δ ppm 8.74 (s, 1H), 8.03 (s, 1H), 7.72 (d, J=7.1 Hz, 1H), 7.29 (m, 2H), 7.16 (d, J=8.5 Hz, 1H), 6.77 (m, 2H), 6.66 (dd; J=10.5, 7.8 Hz; 1H), 4.97 (m, 1H), 4.01 (s, 3H), 2.40 (m, 1H), 2.12-2.30 (m, 4H), 1.65-1.99 (m, 3H). MS (ESI$^+$) m/z 381 (M+H).

Example 5

1-(6,7-dimethylspiro[chroman-2,1'-cyclohexane]-4-yl)-3-(1H-indazol-4-yl)urea

Example 5A 6,7-dimethylspiro[chroman-2,1'-cyclohexan]-4-one

The title compound was prepared using the procedure as described in Example 1A, substituting 4',5'-dimethyl-2'-hydroxyacetophenone (Acros, CAS#36436-65-4) for 2'-hydroxyacetophenone. $^1$H NMR (300 MHz, DMSO-$d_6$) δ 7.44 (s, 1H), 6.84 (s, 1H), 2.68 (s, 2H), 2.23 (s, 3H), 2.16 (s, 3H), 1.80-1.87 (m, 2H), 1.42-1.62 (m, 10H). MS (DCI$^+$) m/z 245 (M+H), 262 (M+NH$_4$).

Example 5B 6,7-dimethylspiro[chroman-2,1'-cyclohexan]-4-amine

The title compound was prepared using the procedure as described in Example 1B, substituting Example 5A for Example 1A. $^1$H NMR (300 MHz, DMSO-$d_6$) δ ppm 7.23 (s, 1H), 6.49 (s, 1H), 3.78 (m, 1H), 2.02 (m, 2H), 1.59-1.73 (m, 2H), 1.24-1.53 (m, 8H). MS (DCI$^+$) m/z 246 (M+H).

Example 5C methyl 4-(3-(6,7-dimethylspiro[chroman-2,1'-cyclohexane]-4-yl)ureido)-1H-indazole-1-carboxylate The title compound was prepared using the procedure as described in Example 1C, substituting Example 5B for Example 1B. The crude compound was then used without further purification.

Example 5D 1-(6,7-dimethylspiro[chroman-2,1'-cyclohexane]-4-yl)-3-(1H-indazol-4-yl)urea The title compound was prepared using the procedure as described in Example 1D, substituting Example 5C for Example 1C. $^1$H NMR (300 MHz, DMSO-$d_6$) δ ppm 13.01 (br, 1H), 8.65 (s, 1H), 8.06 (s, 1H), 7.69 (d, J=7.5 Hz, 1H), 7.22 (t, J=8.0 Hz, 1H), 7.06 (m, 2H), 6.66 (d, J=8.1 Hz, 1H), 6.61 (s, 1H), 4.93 (m, 1H), 2.21 (dd; J=13.9, 6.1 Hz; 1H), 2.14 (s, 3H), 2.12 (s, 3H), 1.62-1.77 (m, 4H), 1.44-1.61 (m, 7H). MS (ESI$^+$) m/z 405 (M+H).

Example 6

1-(6,8-dichlorospiro[chroman-2,1'-cyclohexane]-4-yl)-3-(1H-indazol-4-yl)urea

Example 6A 6,8-dichlorospiro[chroman-2,1'-cyclohexan]-4-one

The title compound was prepared using the procedure as described in Example 1A, substituting 3,5-dichloro-2-hydroxyacetophenone (Lancaster, CAS#3321-92-4) for 2'-hydroxyacetophenone. $^1$H NMR (300 MHz, DMSO-$d_6$) δ ppm 7.92 (d, J=2.4 Hz, 1H), 7.62 (d, J=2.4 Hz, 1H), 2.87 (s, 2H), 1.91 (m, 2H), 1.47-1.68 (m, 8H). MS (DCI$^+$) m/z 284 (M+H).

Example 6B 6,8-dichlorospiro[chroman-2,1'-cyclohexan]-4-amine

A mixture of Example 6A (1.001 g, 3.51 mmol), methoxylamine hydrochloride (293 mg, 3.51 mmol), and pyridine (1.4 mL, 17.3 mmol) in methanol (25 mL) was stirred overnight at room temperature. After this time, the solvent was evaporated in vacuo, and the residue was dissolved in ether and washed with water and brine. The organic layer was dried (Na$_2$SO$_4$), filtered and evaporated in vacuo, and the residue further dried azeotropically (CH$_3$CN). A solution of the residue in tetrahydrofuran (4 mL) was cooled to 0° and was then treated slowly with 1M BH$_3$-tetrahydrofuran (5 mL, 5 mmol). After the addition was complete, the reaction was refluxed for 2.5 h. The mixture was cooled to room temperature and was treated carefully with H$_2$O (3 mL) and 20% aq. KOH (3 mL), then was refluxed for 1 h. The mixture was cooled and extracted with ethyl acetate. The organic extracts were washed with 1N HCl. The aqueous layer was basified with 2M NaOH, followed by extraction with ethyl acetate, afforded the title compound as a yellow oil, 64 mg (6%). $^1$H NMR (300 MHz, DMSO-$d_6$) δ ppm 7.55 (dd; J=14.9, 2.7 Hz; 1H), 7.36 (m, 1H), 3.82 (m, 1H), 2.11 (m, 2H), 1.20-1.82 (m, 10H). MS (DCI$^+$) m/z 286 (M+H).

Example 6C methyl 4-(3-(6,8-dichlorospiro[chroman-2,1'-cyclohexane]-4-yl)ureido)-1H-indazole-1-carboxylate The title compound was prepared using the procedure as described in Example 1C, substituting Example 6B for Example 1B. The crude compound was then used without further purification.

Example 6D 1-(6,8-dichlorospiro[chroman-2,1'-cyclohexane]-4-yl)-3-(1H-indazol-4-yl)urea The title compound was prepared using the procedure as described in Example 1D, substituting Example 6C for Example 1C. $^1$H NMR (300 MHz, DMSO-$d_6$) δ ppm 13.00 (br, 1H), 8.83 (s, 1H), 8.10 (s, 1H), 7.64 (d, J=7.7 Hz, 1H), 7.47 (d, J=2.5 Hz, 1H), 7.29 (m, 1H), 7.23 (t, J=8.0 Hz, 1H), 7.09 (d, J=8.3 Hz, 1H), 6.90 (d, J=4.3 Hz, 1H), 5.05 (m, 1H), 2.23 (dd; J=13.4, 6.6 Hz; 1H), 1.74-1.85 (m, 4H), 1.43-1.66 (m, 7H). MS (ESI$^+$) m/z 445 (M+H).

Example 7

1-(6-chlorospiro[chroman-2,1'-cyclohexane]-4-yl)-3-(1H-indazol-4-yl)urea

Example 7A 6-chlorospiro[chroman-2,1'-cyclohexan]-4-one

The title compound was prepared using the procedure as described in Example 1A, substituting 5'-chloro-2'-hydroxyacetophenone (Aldrich, CAS#1450-74-4) for 2'-hydroxyacetophenone. $^1$H NMR (300 MHz, DMSO-$d_6$) δ ppm 7.64 (d, J=2.7 Hz, 1H), 7.60 (dd; J=8.6, 2.7 Hz; 1H), 7.09 (d, J=9.2 Hz, 1H), 2.80 (s, 2H), 1.85 (m, 2H), 1.45-1.60 (m, 8H). MS (DCI$^+$) m/z 251 (M+H), 268 (M+NH$_4$).

Example 7B 6-chlorospiro[chroman-2,1'-cyclohexan]-4-amine

The title compound was prepared using the procedure as described in Example 6B, substituting Example 7A for Example 6A. $^1$H NMR (300 MHz, DMSO-$d_6$) δ ppm 7.58 (d, J=2.7 Hz, 1H), 7.08 (dd; J=8.8, 2.7 Hz; 1H), 6.71 (d, J=8.8 Hz, 1H), 3.81 (m, 1H), 2.05-2.11 (m, 1H), 1.15-1.74 (m, 11H). MS (DCI$^+$) m/z 252 (M+H).

Example 7C methyl 4-(3-(6-chlorospiro[chroman-2,1'-cyclohexane]-4-yl)ureido)-1H-indazole-1-carboxylate The title compound was prepared using the procedure as described in Example 1C, substituting Example 7B for Example 1B. The crude compound was then used without further purification.

Example 7D 1-(6-chlorospiro[chroman-2,1'-cyclohexane]-4-yl)-3-(1H-indazol-4-yl)urea The title compound was prepared using the procedure as described in Example 1D, substituting Example 7C for Example 1C. $^1$H NMR (300 MHz, DMSO-$d_6$) δ ppm 13.02 (br, 1H), 8.79 (s, 1H), 8.10 (s, 1H), 7.67 (d, J=7.4 Hz, 1H), 7.28 (m, 1H), 7.18-7.23 (m, 2H), 7.09 (d, J=8.5 Hz, 1H), 6.82-6.88 (m, 2H), 5.01 (m, 1H), 2.26 (m, 1H), 1.72 (m, 4H), 1.35-1.76 (m, 7H). MS (ESI+) m/z 411 (M+H).

Example 8

1-(7-tert-butylspiro[chroman-2,1'-cyclobutane]-4-yl)-3-(1H-indazol-4-yl)urea

Example 8A

4'-tert-butyl-2'hydroxyacetophenone

A mixture of 3-tert-butylphenol (4.8 g, 32 mmol) and sodium acetate (6.5 g) was refluxed in acetic anhydride (27 mL) for 3 h. After cooling to room temperature, the mixture was poured into water and extracted with ether. The ethereal extracts were then stirred vigorously with solid $K_2CO_3$ overnight. Filtration, followed by drying over $Na_2SO_4$ and evaporation in vacuo, afforded the corresponding crude acetate as a pale yellow oil, which was used directly without further purification.

To this crude acetate (5.96 g, 31.0 mmol) was added $AlCl_3$ (7.16 g, 53.7 mmol), and the mixture was heated with mechanical stirring at 120° C. for 2.5 h. The reaction mixture was then cooled to rt and was quenched carefully with $H_2O$ and 6N HCl. Extraction with ether, followed by silica gel chromatography (95:5 hexane-ethyl acetate to 9:1 hexane-ethyl acetate, eluant gradient), afforded the title compound as a thick yellow oil, 2.165 g (36%). $^1$H NMR (300 MHz, DMSO-$d_6$) δ ppm 12.01 (br, 1H), 7.81 (d, J=8.5 Hz, 1H), 7.01 (dd, J=8.5, 2.0 Hz, 1H), 6.91 (d, J=2.0 Hz, 1H), 2.61 (s, 2H), 1.27 (s, 9H). MS (ESI) m/z 193 (M+H).

Example 8B 7-tert-butylspiro[chroman-2,1'-cyclobutan]-4-one

The title compound was prepared using the procedure as described in Example 1A, substituting Example 8A for 2'-hydroxyacetophenone and cyclobutanone for cyclohexanone. $^1$H NMR (300 MHz, DMSO-$d_6$) δ ppm 7.64 (d, J=8.4 Hz, 1H), 7.11 (dd; J=8.5, 1.7 Hz; 1H), 6.99 (d, J=1.7 Hz, 1H), 2.92 (s, 2H), 2.08-2.26 (m, 4H), 1.76 (m, 2H), 1.27 (s, 9H). MS (DCI+) m/z 245 (M+H), 262 (M+NH$_4$).

Example 8C 7-tert-butylspiro[chroman-2,1'-cyclobutan]-4-amine

The title compound was prepared using the procedure as described in Example 1B, substituting Example 8B for Example 1A. $^1$H NMR (300 MHz, DMSO-$d_6$) δ ppm 7.41 (d, J=8.5 Hz, 1H), 7.03 (dd; J=8.1, 2.1 Hz; 1H), 6.82 (d, J=2.0 Hz, 1H), 4.51 (m, 1H), 1.99-2.21 (m, 3H), 1.65-1.91 (m, 5H), 1.24 (s, 9H). MS (DCI+) m/z 246 (M+H).

Example 8D methyl 4-(3-(7-tert-butylspiro[chroman-2,1'-cyclobutane]-4-yl)ureido)-1H-indazole-1-carboxylate The title compound was prepared using the procedure as described in Example 1C, substituting Example 8C for Example 1B. The crude compound was then used without further purification.

Example 8E 1-(7-tert-butylspiro[chroman-2,1'-cyclobutane]-4-yl)-3-(1H-indazol-4-yl)urea The title compound was prepared using the procedure as described in Example 1D, substituting Example 8D for Example 1C. $^1$H NMR (300 MHz, DMSO-$d_6$) δ ppm 13.01 (br, 1H), 8.66 (s, 1H), 8.05 (s, 1H), 7.69 (d, J=7.1 Hz, 1H), 7.20 (m, 2H), 7.08 (d, J=8.5 Hz, 1H), 6.96 (dd; J=7.7, 1.8 Hz; 1H), 6.78 (d, J=2.0 Hz, 1H), 6.74 (d, J=7.8 Hz, 1H), 4.94 (m, 1H), 2.14-2.41 (m, 3H), 1.75-1.99 (m, 5H), 1.24 (s, 9H). MS (ESI+) m/z 405 (M+H), 427 (M+Na).

Example 9

1-(6,8-difluorospiro[chroman-2,1'-cyclohexane]-4-yl)-3-(1H-indazol-4-yl)urea

Example 9A 6,8-difluorospiro[chroman-2,1'-cyclohexan]-4-one

The title compound was prepared using the procedure as described in Example 1A, substituting 3,5-difluoro-2-hydroxyacetophenone (Apollo, CAS#140675-42-9) for 2'-hydroxyacetophenone. $^1$H NMR (300 MHz, DMSO-$d_6$) δ ppm 7.65-7.72 (m, 1H), 7.23-7.31 (m, 1H), 7.14-7.19 (m, 1H), 2.88 (s, 2H), 1.89 (m, 2H), 1.46-1.62 (m, 8H). MS (DCI+) m/z 253 (M+H).

Example 9B 6,8-difluoro spiro[chroman-2,1'-cyclohexan]-4-amine

The title compound was prepared using the procedure as described in Example 6B, substituting Example 9A for Example 6A. $^1$H NMR (300 MHz, DMSO-$d_6$) δ ppm 7.20-7.25 (m, 1H), 7.01-7.08 (m, 1H), 3.79-3.85 (m, 1H), 2.11 (m, 1H), 1.33-1.73 (m, 11H). MS (DCI+) m/z 254 (M+H), 271 (M+NH$_4$).

Example 9C methyl 4-(3-(6,8-difluorospiro[chroman-2,1'-cyclohexane]-4-yl)ureido)-1H-indazole-1-carboxylate The title compound was prepared using the procedure as described in Example 1C, substituting Example 9B for Example 1B. The crude compound was then used without further purification.

Example 9D 1-(6,8-difluorospiro[chroman-2,1'-cyclohexane]-4-yl)-3-(1H-indazol-4-yl)urea The title compound was prepared using the procedure as described in Example 1D, substituting Example 9C for Example 1C. $^1$H NMR (300 MHz, DMSO-$d_6$) δ ppm 13.00 (br, 1H), 8.76 (s, 1H), 8.08 (s, 1H), 7.64 (s, 1H), 7.16-7.25 (m, 2H), 7.09 (d, J=8.3 Hz, 1H), 6.97 (m, 1H), 6.83 (d, J=8.3 Hz, 1H), 5.01 (m, 1H), 2.29 (m, 1H), 1.66-1.82 (m, 5H), 1.44-1.63 (m, 6H). MS (ESI) m/z 413 (M+H), 435 (M+Na).

Example 10

1-(6-ethoxyspiro[chroman-2,1'-cyclohexane]-4-yl)-3-(1H-indazol-4-yl)urea

Example 10A

6-ethoxyspiro[chroman-2,1'-cyclohexan]-4-one

The title compound was prepared using the procedure as described in Example 1A, substituting 5'-ethoxy-2'-hydroxyacetophenone (Aldrich, CAS#56414-14-3) for 2'-hydroxyacetophenone. $^1$H NMR (300 MHz, DMSO-$d_6$) δ ppm 7.13-7.18 (m, 2H), 6.95 (d, J=8.4 Hz, 1H), 3.99 (q, J=7.1 Hz, 2H), 2.73 (s, 2H), 1.74-1.86 (m, 2H), 1.39-1.66 (m, 8H), 1.30 (t, J=7.1 Hz, 3H). MS (DCI$^+$) m/z 261 (M+H), 278 (M+NH$_4$).

Example 10B

6-ethoxyspiro[chroman-2,1'-cyclohexan]-4-amine

A mixture of Example 10A (1.182 g, 4.55 mmol), methoxylamine hydrochloride (380 mg, 4.55 mmol), and pyridine (1.8 mL, 22.3 mmol) in methanol (15 mL) was stirred overnight at room temperature. After this time, the solvent was evaporated in vacuo, then the residue was dissolved in ether and washed with water and brine. The organic layer was dried (Na$_2$SO$_4$), filtered and was evaporated in vacuo, and the residue was further dried azeotropically (CH$_3$CN). A solution of the residue (942 mg, 3.26 mmol) in tetrahydrofuran (10 mL) was treated slowly with 1M LiAlH$_4$ in tetrahydrofuran (5 mL, 5 mmol). After the addition was complete, the reaction was refluxed for 2.5 h. The mixture was cooled to room temperature and carefully quenched with water and was then filtered. The filter pad was washed with ethyl acetate, and the combined filtrates were evaporated in vacuo to afford a gold oil. This was taken up in ether and extracted with 1N HCl, then the acidic extracts were basified with 2N NaOH and were extracted with ethyl acetate. Drying of the organic extracts (Na$_2$SO$_4$), filtered, followed by evaporation in vacuo, afforded the title compound as a gold oil, 320 mg (38%). $^1$H NMR (300 MHz, DMSO-$d_6$) δ ppm 7.10 (d, J=2.7 Hz, 1H), 6.58-6.66 (m, 2H), 3.93 (q, J=7.1 Hz, 2H), 3.78 (m, 1H), 2.04 (m, 1H), 1.36-1.77 (m, 11H), 1.17 (t, J=7.0 Hz, 3H). MS (DCI$^+$) m/z 262 (M+H).

Example 10C methyl 4-(3-(6-ethoxyspiro[chroman-2,1'-cyclohexane]-4-yl)ureido)-1H-indazole-1-carboxylate The title compound was prepared using the procedure as described in Example 1C, substituting Example 10B for Example 1B. The crude compound was then used without further purification.

Example 10D

1-(6-ethoxyspiro[chroman-2,1'-cyclohexane]-4-yl)-3-(1H-indazol-4-yl)urea

The title compound was prepared using the procedure as described in Example 1D, substituting Example 10C for Example 1C. $^1$H NMR (300 MHz, DMSO-$d_6$) δ ppm 12.99 (br, 1H), 8.72 (s, 1H), 8.08 (d, J=1.0 Hz, 1H), 7.68 (dd; J=7.8, 1.5 Hz; 1H), 7.21 (m, 2H), 7.08 (d, J=8.1 Hz, 1H), 6.84 (m, 1H), 6.76 (m, 2H), 4.94 (m, 1H), 3.92 (q, J=7.1 Hz, 2H), 2.23 (m, 1H), 1.71 (m, 4H), 1.42-1.59 (m, 7H), 1.26 (t, J=7.1 Hz, 3H). MS (ESI$^+$) 421 (M+H).

Example 11

1-(1H-indazol-4-yl)-3-(6-methylspiro[chroman-2,1'-cyclopentane]-4-yl)urea

Example 11A

6-methylspiro[chroman-2,1'-cyclopentan]-4-one

The title compound was prepared using the procedure as described in Example 1A, substituting 2'-hydroxy-5'-methylacetophenone (Aldrich, CAS#1450-72-2) for 2'-hydroxyacetophenone and cyclopentanone for cyclohexanone. $^1$H NMR (300 MHz, DMSO-$d_6$) δ ppm 7.51 (m, 1H), 7.35 (m, 1H), 6.87 (d, J=8.5 Hz, 1H), 2.85 (s, 2H), 2.26 (s, 3H), 1.89-1.95 (m, 2H), 1.59-1.79 (m, 6H). MS (DCI$^+$) m/z 217 (M+H), 234 (M+NH$_4$).

Example 11B

6-methylspiro[chroman-2,1'-cyclopentan]-4-amine

The title compound was prepared using the procedure as described in Example 10B, substituting Example 11A for Example 10A. $^1$H NMR (300 MHz, DMSO-$d_6$) δ ppm 6.84 (m, 2H), 6.54 (m, 1H), 3.78 (m, 1H), 2.25 (m, 1H), 2.17 (s, 3H), 1.43-1.86 (m, 9H). MS (DCI$^+$) m/z 218 (M+H).

Example 11C methyl 4-(3-(6-methylspiro[chroman-2,1'-cyclopentane]-4-yl)ureido)-1H-indazole-1-carboxylate The title compound was prepared using the procedure as described in Example 1C, substituting Example 11B for Example 1B. The crude compound was then used without further purification.

Example 11D

1-(1H-indazol-4-yl)-3-(6-methylspiro[chroman-2,1'-cyclopentane]-4-yl)urea

The title compound was prepared using the procedure as described in Example 1D, substituting Example 11C for Example 1C. $^1$H NMR (300 MHz, DMSO-$d_6$) δ ppm 13.00 (br, 1H), 8.70 (s, 1H), 8.07 (s, 1H), 7.70 (d, J=7.1 Hz, 1H), 7.22 (m, 2H), 7.11 (m, 1H), 6.96 (m, 1H), 6.75 (d, J=6.8 Hz, 1H), 6.64 (d, J=7.9 Hz, 1H), 4.97 (m, 1H), 2.21 (s, 3H), 2.18 (m, 1H), 1.39-1.83 (m, 9H). MS (ESI$^+$) 377 (M+H), 399 (M+Na).

Example 12

1-(7-ethoxyspiro[chroman-2,1'-cyclopentane]-4-yl)-3-(1H-indazol-4-yl)urea

Example 12A

7-ethoxyspiro[chroman-2,1'-cyclopentan]-4-one

The title compound was prepared using the procedure as described in Example 1A, substituting 4'-ethoxy-2'-hydroxyacetophenone (Aldrich, CAS#37470-42-1) for 2'-hydroxyacetophenone and cyclopentanone for cyclohexanone. $^1$H NMR (300 MHz, DMSO-$d_6$) δ ppm 7.65 (d, J=8.6 Hz, 1H), 6.57 (dd; J=8.4, 2.3 Hz; 1H), 6.45 (d, J=2.4 Hz, 1H), 4.08 (q, J=7.1 Hz, 2H), 2.79 (s, 2H), 1.94 (m, 2H), 1.60-1.80 (m, 6H), 1.32 (t, J=7.0 Hz, 3H). MS (DCI$^+$) m/z 247 (M+H), 264 (M+NH$_4$).

Example 12B 7-ethoxyspiro[chroman-2,1'-cyclopentan]-4-amine

The title compound was prepared using the procedure as described in Example 10B, substituting Example 12A for Example 10A, and was used without further purification.

Example 12C methyl 4-(3-(7-ethoxyspiro[chroman-2,1'-cyclopentane]-4-yl)ureido)-1H-indazole-1-carboxylate The title compound was prepared using the procedure as described in Example 1C, substituting Example 12B for Example 1B. The crude compound was then used without further purification.

Example 12D 1-(7-ethoxyspiro[chroman-2,1'-cyclopentane]-4-yl)-3-(1H-indazol-4-yl)urea The title compound was prepared using the procedure as described in Example 1D, substituting Example 12C for Example 1C. $^1$H NMR (300 MHz, DMSO-$d_6$) δ ppm 12.99 (br, 1H), 8.67 (s, 1H), 8.06 (s, 1H), 7.68 (d, J=7.0 Hz, 1H), 7.19 (m, 2H), 7.07 (d, J=8.3 Hz, 1H), 6.66 (d, J=6.3 Hz, 1H), 6.50 (dd; J=8.5, 2.5 Hz; 1H), 6.28 (d, J=2.5 Hz, 1H), 4.92 (m, 1H), 3.97 (q, J=7.0 Hz, 2H), 2.18 (m, 1H), 1.94 (m, 1H), 1.61-1.84 (m, 8H), 1.29 (t, J=7.1 Hz, 3H). MS (ESI) m/z 407 (M+H), 429 (M+Na).

Example 13

1-(6,7-dimethylspiro[chroman-2,1'-cyclopentane]-4-yl)-3-(1H-indazol-4-yl)urea

Example 13A 6,7-dimethylspiro[chroman-2,1'-cyclopentan]-4-one

The title compound was prepared using the procedure as described in Example 1A, substituting 4',5'-dimethyl-2'-hydroxyacetophenone (Acros, CAS#36436-65-4) for 2'-hydroxyacetophenone and cyclopentanone for cyclohexanone. $^1$H NMR (300 MHz, DMSO-$d_6$) δ ppm 7.46 (s, 1H), 6.79 (s, 1H), 2.80 (s, 2H), 2.22 (s, 3H), 2.17 (s, 3H), 1.90 (m, 2H), 1.66 (m, 6H). MS (DCI$^+$) m/z 231 (M+H), 248 (M+NH$_4$).

Example 13B 6,7-dimethylspiro[chroman-2,1'-cyclopentan]-4-amine

The title compound was prepared using the procedure as described in Example 10B, substituting Example 13A for Example 10A. $^1$H NMR (300 MHz, DMSO-$d_6$) δ ppm 6.69 (m, 1H), 6.45 (m, 1H), 3.75 (m, 1H), 2.24 (m, 1H), 2.11 (s, 3H), 2.07 (s, 3H), 1.41-1.86 (m, 9H).

Example 13C methyl 4-(3-(6,7-dimethylspiro[chroman-2,1'-cyclopentane]-4-yl)ureido)-1H-indazole-1-carboxylate The title compound was prepared using the procedure as described in Example 1C, substituting Example 13B for Example 1B. The crude compound was then used without further purification.

Example 13D 1-(6,7-dimethylspiro[chroman-2,1'-cyclopentane]-4-yl)-3-(1H-indazol-4-yl)urea The title compound was prepared using the procedure as described in Example 1D, substituting Example 13C for Example 1C. $^1$H NMR (300 MHz, DMSO-$d_6$) δ ppm 13.01 (br, 1H), 8.67 (s, 1H), 8.06 (s, 1H), 7.70 (d, J=7.1 Hz, 1H), 7.22 (m, 1H), 7.07 (d, J=8.2 Hz, 1H), 7.05 (s, 1H), 6.68 (d, J=7.8 Hz, 1H), 6.56 (s, 1H), 4.92 (m, 1H), 2.19 (m, 1H), 2.14 (s, 3H), 2.12 (s, 3H), 1.93 (m, 1H), 1.55-1.84 (m, 8H). MS (ESI$^+$) 391 (M+H), 413 (M+Na).

Example 14

1-(7-fluorospiro[chroman-2,1'-cyclohexane]-4-yl)-3-(1-methyl-1H-indazol-4-yl)urea The title compound was prepared using the procedure as described in Example 4, substituting Example 2D for Example 3D. $^1$H NMR (300 MHz, DMSO-$d_6$) δ 8.71 (s, 1H), 8.03 (d, J=1.1 Hz, 1H), 7.70 (dd; J=7.9, 1.1 Hz; 1H), 7.25-7.35 (m, 2H), 7.17 (d, J=8.5 Hz, 1H), 6.62-6.78 (m, 3H), 4.94 (m, 1H), 4.00 (s, 3H), 2.23 (m, 1H), 1.51-1.75 (m, 11H). MS (ESI) m/z 409 (M+H), 431 (M+Na).

Example 15

1-(1-methyl-1H-indazol-4-yl)-3-(spiro[chroman-2,1'-cyclohexane]-4-yl)urea

The title compound was prepared using the procedure as described in Example 4, substituting Example 1D for Example 3D. $^1$H NMR (300 MHz, DMSO-$d_6$) δ 8.70 (s, 1H), 8.03 (d, J=1.1 Hz, 1H), 7.72 (d, J=7.5 Hz, 1H), 7.25-7.32 (m, 2H), 7.16 (m, 2H), 6.90 (m, 1H), 6.80 (d, J=8.1 Hz, 1H), 6.71 (d, J=8.8 Hz, 1H), 4.99 (m, 1H), 4.00 (s, 3H), 2.26 (m, 1H), 1.42-1.77 (m, 11H). MS (ESI) m/z 391 (M+H).

Example 16

1-(1H-indazol-4-yl)-3-(7-methoxyspiro[chroman-2,1'-cyclohexane]-4-yl)urea

Example 16A 7-hydroxyspiro[chroman-2,1'-cyclohexane]-4-one

To a solution of diethyl phosphite (4 mL, 31.0 mmol) in 1,2-dimethoxyethane (100 mL) was added 60% NaH (3.72 g, 93 mmol). When gas evolution had mostly ceased (10 min), a solution of bromoacetic acid (4.3 g, 30.9 mmol) in 1,2-dimethoxyethane (30 mL) was added slowly. When gas evolution had again ceased, cyclohexanone (3.2 mL, 30.9 mmol) was added dropwise. The reaction mixture was stirred at room temperature for 1 h, then was quenched with ethanol (5 mL) and was poured into ice water. The aqueous layer was washed with ether, acidified to pH 4 with conc. HCl, and then extracted with ether. The extracts were dried over $Na_2SO_4$, filtered and were evaporated in vacuo. The title compound was afforded as a yellow-orange oil, which was mixed in $POCl_3$ (25 mL, 268.2 mmol) with resorcinol (3.39 g, 30.8 mmol) and $ZnCl_2$ (5.9 g, 43.3 mmol). The mixture was stirred at room temperature for 5.5 h and was then poured onto ice. Extraction with ethyl acetate, followed by drying over $Na_2SO_4$, filtration and evaporation in vacuo, afforded the crude product as a dark orange oil. Chromatography on silica gel (7:3 hexane-ethyl acetate, eluant) yielded the title compound as an off-white solid, 3.14 g (44%). $^1$H NMR (300 MHz, DMSO-$d_6$) δ 10.47 (br, 1H), 7.56 (d, J=8.5 Hz, 1H), 6.43 (m, 1H), 6.28 (d, J=2.4 Hz, 1H), 2.63 (s, 2H), 1.44-1.87 (m, 10H). MS (DCI$^+$) m/z 233 (M+H).

Example 16B 7-hydroxyspiro[chroman-2,1'-cyclohexan]-4-one O-methyl oxime

The product from Example 16A (479 mg, 2.06 mmol), methoxylamine hydrochloride (275 mg, 3.29 mmol), and pyridine (0.36 mL, 4.45 mmol) were stirred in methanol (5 mL) at room temperature overnight. After this time, the solvent was evaporated in vacuo, and the residue was taken up in ethyl acetate and washed with 1N HCl and brine. The organic solution was dried over $Na_2SO_4$ and was evaporated in vacuo. Chromatography on silica gel (4:1 hexane-ethyl acetate, eluant) afforded the title compound as a colorless oil, 524 mg (97%). $^1$H NMR (300 MHz, DMSO-$d_6$) δ 9.79 (br, 1H), 7.54 (d, J=8.8 Hz, 1H), 6.35 (m, 1H), 6.22 (m, 1H), 3.84 (s, 3H), 2.68 (s, 2H), 1.25-1.79 (m, 10H). MS (DCI$^+$) m/z 262 (M+H).

Example 16C 7-methoxyspiro[chroman-2,1'-cyclohexan]-4-amine

The product from 16B (0.169 g, 0.647 mmol) was stirred with MeI (0.080 mL, 1.3 mmol) and $K_2CO_3$ (0.267 g, 1.93 mmol) in acetone (2 mL) at 65 C overnight. The solvent was evaporated and the residue was dissolved in ethyl acetate, washed with water then with brine, and then dried ($Na_2SO_4$) and concentrated. The crude material was dissolved in methanol (5 mL) and shaken with Raney-Nickel (300 mg) under $H_2$ (60 psi) overnight. The mixture was filtered and evaporated to give 0.195 g of the crude amine as a filmy, white solid, which was taken on without further purification.

Example 16D 1-(1H-indazol-4-yl)-3-(7-methoxyspiro[chroman-2, 1'-cyclohexane]-4-yl)urea The product of Example 16C (0.195 g) was stirred with the product of Example 1H (0.215 g, 0.647 mmol) and diisopropylethylamine (0.15 mL, 0.86 mmol) in 2 mL N,N-dimethylformamide at room temperature for 1 h. After this time, the mixture was diluted with $H_2O$. The precipitate thus formed was collected by filtration, dissolved in methanol (2 mL) and tetrahydrofuran (0.5 mL), and treated with 1N aq NaOH (0.75 mL, 0.75 mmol). The mixture was stirred at room temperature for 3 h, and precipitated with $H_2O$. The precipitate was dissolved in ethyl acetate, and washed with water, and brine, and dried ($Na_2SO_4$) and evaporated to give the product as a tan solid (0.219 g, 0.540 mmol, 83%). $^1$H NMR (300 MHz, DMSO-$d_6$) δ ppm 13.01 (br s, 1H), 8.65 (s, 1H), 8.06 (br s, 1H), 7.68 (d, 1H), 7.21 (m, 2H), 7.07 (d, 1H), 6.64 (d, 1H), 6.51 (dd, 1H), 6.35 (d, 1H), 4.92 (m, 1H), 3.71 (s, 3H), 2.22 (dd, 1H), 1.25-1.80 (m, 12H); MS (ESI$^+$) m/z 407.2 (M+H).

Example 17

1-(1H-indazol-4-yl)-3-(1'-methylspiro[chroman-2,4'-piperidine]-4-yl)urea

Example 17A

1'-methylspiro[chroman-2,4'-piperidin]-4-one

The title compound was prepared using the procedure as described in Example 1A, substituting 1-methyl-4-piperidone for cyclohexanone. 1 NMR (300 MHz, DMSO-$d_6$) δ 7.72 (dd; J=7.9, 1.7 Hz; 1H), 7.56 (m, 1H), 7.00-7.05 (m, 2H), 2.79 (s, 2H), 2.45 (m, 1H), 2.23-2.37 (m, 3H), 2.18 (s, 3H), 1.83-1.93 (m, 2H), 1.65-1.77 (m, 2H). MS (DCI$^+$) m/z 232 (M+H).

Example 17B

1'-methylspiro[chroman-2,4'-piperidin]-4-amine

The title compound was prepared using the procedure as described in Example 1B, substituting Example 17A for Example 1A. $^1$H NMR (300 MHz, DMSO-$d_6$) δ 7.52 (d, J=7.5 Hz, 1H), 7.06 (m, 1H), 6.84 (td; J=7.5, 1.1 Hz; 1H), 6.70 (dd; J=8.2, 1.0 Hz; 1H), 3.85 (m, 1H), 2.35-2.55 (m, 2H), 2.18 (s, 3H), 2.16 (m, 1H), 1.99-2.05 (m, 2H), 1.47-1.72 (m, 5H). MS (DCI$^+$) m/z 233 (M+H).

Example 17C

Methyl 4-(3-(1'-methylspiro[chroman-2,4'-piperidine]-4-yl)ureido)-1H-indazole-1-carboxylate The title compound was prepared using the procedure as described in Example 1C, substituting Example 17B for Example 1B. The crude compound was then used without further purification.

Example 17D 1-(1H-indazol-4-yl)-3-(1'-methylspiro[chroman-2,4'-piperidine]-4-yl)urea The title compound was prepared using the procedure as described in Example 1D, substituting Example 17C for Example 1C. $^1$H NMR (300 MHz, DMSO-$d_6$) δ 13.02 (br, 1H), 8.73 (s, 1H), 8.07 (s, 1H), 7.68 (d, J=7.5 Hz, 1H), 7.14-7.33 (m, 3H), 7.08 (d, J=8.1 Hz, 1H), 6.91 (t, J=7.5 Hz, 1H), 6.77-6.82 (m, 2H), 5.01 (m, 1H), 2.56 (m, 2H), 2.38 (m,

Example 18

1-(1H-indazol-4-yl)-3-(2',3',5',6'-tetrahydrospiro[chroman-2,4'-pyran]-4-yl)urea

Example 18A

2',3',5',6'-tetrahydrospiro[chroman-2,4'-pyran]-4-one

The title compound was prepared using the procedure as described in Example 1A, substituting tetrahydro-4H-pyran-4-one for cyclohexanone. 1 NMR (300 MHz, DMSO-$d_6$) δ 7.71 (dd; J=7.8, 1.7 Hz; 1H), 7.58 (m, 1H), 7.02-7.10 (m, 2H), 3.63-3.73 (m, 4H), 2.85 (s, 2H), 1.70-1.87 (m, 4H). MS (DCI$^+$) m/z 219 (M+H), 236 (M+NH$_4$).

Example 18B

2',3',5',6'-tetrahydrospiro[chroman-2,4'-pyran]-4-amine

The title compound was prepared using the procedure as described in Example 1B, substituting Example 18A for Example 1A. $^1$H NMR (300 MHz, DMSO-$d_6$) δ 7.53 (d, J=7.5 Hz, 1H), 7.08 (m, 1H), 6.85 (td; J=7.5, 1.4 Hz; 1H), 6.75 (dd; J=8.1, 1.0 Hz; 1H), 3.87 (m, 1H), 3.56-3.82 (m, 4H), 2.10 (m, 1H), 1.76 (m, 1H), 1.50-1.69 (m, 4H). MS (DCI$^+$) m/z 220 (M+H).

Example 18C

Methyl-4-(3-(2',3',5',6'-tetrahydrospiro[chroman-2,4'-pyran]-4-yl)ureido)-1H-indazole-1-carboxylate The title compound was prepared using the procedure as described in Example 1C, substituting Example 18B for Example 1B. The crude compound was then used without further purification.

Example 18D 1-(1H-indazol-4-yl)-3-(2',3',5',6'-tetrahydrospiro[chroman-2,4'-pyran]-4-yl)urea The title compound was prepared using the procedure as described in Example 1D, substituting Example 18C for Example 1C. $^1$H NMR (300 MHz, DMSO-$d_6$) δ 13.01 (br, 1H), 8.73 (s, 1H), 8.08 (d, J=0.7 Hz, 1H), 7.68 (d, J=7.1 Hz, 1H), 7.32 (d, J=7.4 Hz, 1H), 7.16-7.25 (m, 2H), 7.08 (d, J=8.4 Hz, 1H), 6.84-6.95 (m, 2H), 6.79 (d, J=8.1 Hz, 1H), 5.03 (m, 1H), 3.61-3.82 (m, 4H), 2.28 (m, 2H), 1.70-1.83 (m, 4H). MS (ESI$^+$) m/z 379 (M+H), 401 (M+Na).

Example 19

1-(7-fluoro-2',3',5',6'-tetrahydrospiro[chroman-2,4'-pyran]-4-yl)-3-(1H-indazol-4-yl)urea

Example 19A 7-fluoro-2',3',5',6'-tetrahydrospiro[chroman-2,4'-pyran]-4-one

The title compound was prepared using the procedure as described in Example 1A, substituting tetrahydro-4H-pyran-4-one for cyclohexanone and 4'-fluoro-2'hydroxyacetophenone for 2'-hydroxyacetophenone. 1 NMR (300 MHz, DMSO-$d_6$) δ ppm 7.80 (dd, J=8.81, 6.78 Hz, 1H), 6.87-7.01 (m, 2H), 3.62-3.74 (m, 4H), 2.86 (s, 2H), 1.73-1.86 (m, 4H). MS (DCI$^+$) m/z 237 (M+H), 254 (M+NH$_4$).

Example 19B 7-fluoro-2',3',5',6'-tetrahydrospiro[chroman-2,4'-pyran]-4-amine The title compound was prepared using the procedure as described in Example 1B, substituting Example 19A for Example 1A. $^1$H NMR (300 MHz, DMSO-$d_6$) δ ppm 7.56 (t, J=7.80 Hz, 1H), 6.69 (td, J=8.65, 2.71 Hz, 1H), 6.58 (dd, J=10.85, 2.71 Hz, 1H), 3.80-3.87 (m, 1H), 3.64-3.78 (m, 2H), 3.55-3.63 (m, 2H), 2.04-2.14 (m, 1H), 1.98 (m, 1H), 1.67-1.77 (m, 2H), 1.60-1.65 (m, 2H). MS (DCI$^+$) m/z 238 (M+H), 255 (M+NH$_4$).

Example 19C methyl 4-(3-(7-fluoro-2',3',5',6'-tetrahydrospiro[chroman-2,4'-pyran]-4-yl)ureido)-1H-indazole-1-carboxylate The title compound was prepared using the procedure as described in Example 1C, substituting Example 19B for Example 1B. The crude compound was then used without further purification.

Example 19D 1-(7-fluoro-2',3',5',6'-tetrahydrospiro[chroman-2,4'-pyran]-4-yl)-3-(1H-indazol-4-yl)urea The title compound was prepared using the procedure as described in Example 1D, substituting Example 19C for Example 1C. $^1$H NMR (300 MHz, DMSO-$d_6$) δ ppm 13.01 (br, 1H), 8.74 (s, 1H), 8.08 (s, 1H), 7.65-7.70 (m, 1H), 7.31-7.37 (m, 1H), 7.17-7.26 (m, 1H), 7.08 (d, J=8.14 Hz, 1H), 6.69-6.81 (m, 3H), 5.01 (s, 1H), 3.69-3.82 (m, 2H), 3.61-3.66 (m, 2H), 2.23-2.31 (m, 2H), 1.69-1.84 (m, 4H). MS (ESI$^+$) m/z 397 (M+H), 419 (M+Na).

Example 20

1-(7-fluoro-2',3',5',6'-tetrahydrospiro[chroman-2,4'-pyran]-4-yl)-3-(1-methyl-1H-indazol-4-yl)urea The title compound was prepared using the procedure as described in Example 4, substituting Example 19D for Example 3D. $^1$H NMR (300 MHz, DMSO-$d_6$) δ ppm 8.76 (s, 1H), 8.04 (s, 1H), 7.68-7.72 (m, 1H), 7.28-7.37 (m, 2H), 7.15-7.19 (m, 1H), 6.72-6.81 (m, 3H), 5.01 (s, 1H), 4.00 (s, 3H), 3.71-3.79 (m, 2H), 3.61-3.69 (m, 2H), 2.23-2.31 (m, 1H), 1.69-1.84 (m, 5H).

Example 21

1-(7-fluoro-2',3',5',6'-tetrahydrospiro[chroman-2,4'-pyran]-4-yl)-3-(2-methyl-2H-indazol-4-yl)urea The title compound was obtained as a by-product in the preparation of Example 20. $^1$H NMR (300 MHz, DMSO-$d_6$) δ ppm 8.55-8.59 (m, 1H), 8.21 (s, 1H), 7.45-7.49 (m, 1H), 7.29-7.36 (m, 1H), 7.08-7.18 (m, 2H), 6.64-6.81 (m, 3H),

[preceding fragment: 2H), 2.22 (m, 1H), 2.20 (s, 3H), 1.63-1.81 (m, 5H). MS (ESI$^+$) m/z 392 (M+H), 414 (M+Na).]

5.01 (s, 1H), 4.16 (s, 3H), 3.69-3.79 (m, 2H), 3.61-3.67 (m, 2H), 2.26 (m, 1H), 1.69-1.84 (m, 5H). MS (ESI+) m/z 411 (M+H), 433 (M+Na).

Biological Activity

In Vitro Data—Determination of Inhibition Potencies

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate) (without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 88: 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ($[Ca^{2+}]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR) (Molecular Devices, Sunnyvale, Calif.). Cells were grown to confluency in 96-well black-walled tissue culture plates. Then, prior to the assay, the cells were loaded with 100 µL per well of fluo-4 AM (2 µM, in D-PBS) for 1-2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3 minute time delay, 50 µL of the capsaicin solution was added at the 190 second time mark (0.05 µM final concentration) (final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$ lower than 1 µM, preferably lower than 0.5 µM, more preferably less than 0.1 µM, and most preferably less than 0.1 µM.

In Vivo Data—Determination of Antinociceptive Effect

Experiments were performed on 400 adult male 129J mice (Jackson Laboratories, Bar Harbor, Me.), weighing 20-25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee. The Complete Freund's Adjuvant-induced Thermal Hyperalgesia (CFA) assay described in Pircio et al. *Eur J. Pharmacol. Vol,* 31(2) pages 207-215 (1975). Chronic inflammatory hyperalgesia was induced in one group of rats following the injection of complete Freund's adjuvant (CFA, 50%, 150 µL) into the plantar surface of the right hindpaw 48 hours prior to testing. Thermal nociceptive thresholds were measured in three different groups of rats. The $ED_{50s}$ were determined based on the oral administration. A compound tested for in vivo activity had an $ED_{50}$ of less than 500 nmol/kg.

The in vitro and in vivo data demonstrates that compounds of the present invention antagonize the VR1 receptor and are useful for treating pain, bladder overactivity, and urinary incontinence.

What is claimed is:

1. A method of treating a disorder selected from the group consisting of pain, neuropathic pain, allodynia, pain associated with inflammation, inflammatory hyperalgesia, bladder overactivity, and urinary incontinence, the method comprising administering to a subject in need thereof a therapeutically effective amount of a compound of formula (I), or a pharmaceutically acceptable salt thereof, wherein

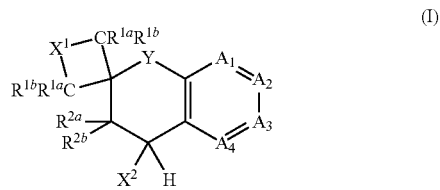

$X^1$ is $—(CR^{1a}R^{1b})_m—$, $—(CR^{1a}R^{1b})_n G^1-$, or $—(CR^{1a}R^{1b})_p-G^1-C(CR^{1a}R^{1b})—$;

m is 1, 2, 3 or 4;

n is 1, 2 or 3;

p is 1 or 2;

$G^1$ is O, N($R^x$), or S;

$R^{1a}$ and $R^{1b}$, at each occurrence, are independently hydrogen, alkyl, halogen, or haloalkyl;

$R^{2a}$ and $R^{2b}$, at each occurrence, are independently hydrogen, alkyl, halogen, or haloalkyl;

$R^x$ is hydrogen, alkyl, haloalkyl, $R^y$, —C(O)Oalkyl, or —C(O)OR$^y$;

$R^y$ at each occurrence is independently arylalkyl or heteroarylalkyl; wherein the aryl moiety of the arylalkyl and the heteroaryl moiety of the heteroarylalkyl are independently unsubstituted or substituted with 1, 2, 3 or 4 substituents independently selected from the group consisting of alkyl, halogen, alkoxy and haloalkyl;

$A_1$ is N or $CR^3$;

$A_2$ is N or $CR^4$;

$A_3$ is N or $CR^5$;

$A_4$ is N or $CR^6$; provided that only one or two of $A_1, A_2, A_3$ and $A_4$ can be N;

$R^3$, $R^4$, $R^5$ and $R^6$ are each independently selected from the group consisting of, hydrogen, alkyl, alkenyl, alkynyl, haloalkyl, halogen, —CN, —NO$_2$, —OH, alkoxy, haloalkoxy, —OR$_E$, —O—(CR$^{1a}$R$^{1b}$)$_q$—R$_E$, —N(R$_A$)(R$_B$), —C(O)R$_B$, —C(O)N(R$_A$)(R$_B$), —C(O)OR$_B$, S(R$_B$), —S(O)R$_B$, —S(O)$_2$R$_B$, —S(O)$_2$N(R$_A$)(R$_B$), R$_E$ and —(CR$^{1a}$R$^{1b}$)$_q$—R$_E$;

q is 1, 2, 3, 4, 5 or 6;

R$_A$ at each occurrence is independently hydrogen, alkyl or haloalkyl;

R$_B$ at each occurrence is independently hydrogen, alkyl, alkenyl, haloalkyl, R$_E$ or —(CR$^{1a}$R$^{1b}$)$_q$—R$_E$;

R$_E$ at each occurrence is independently a monocyclic or bicyclic ring, independently selected from the group consisting of cycloalkyl, cycloalkenyl, heterocycle, heteroaryl and aryl; wherein each R$_E$ is independently unsubstituted or substituted with 1, 2, 3 or 4 substituents selected from the group consisting of alkyl, haloalkyl, halogen, oxo, —CN, —NO$_2$, —OH, alkoxy, haloalkoxy, —NH$_2$, —N(H)(alkyl), —N(alkyl)$_2$, —N(H)C(O)alkyl, —N(alkyl)C(O)alkyl, —N(H)C(O)Oalkyl, —N(alkyl)C(O)Oalkyl, —C(O)H, —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$;

Y is —S—, —S(O), —S(O)$_2$, —O—, —N(R$^7$)— or —C(R$^{1a}$R$^{1b}$)—;

$R^7$ is hydrogen, alkyl, alkenyl, alkoxy, haloalkyl, —C(O)OR$_B$, R$_E$, or —(CR$^{1a}$R$^{1b}$)$_q$—R$_E$;

$X^2$ is —N(H)C(O)N(H)—Z or —(CR$^g$R$^h$)$_q$—N(H)C(O)N(H)—Z;

$R^g$ and $R^h$ are independently hydrogen or alkyl; and

Z is a monocyclic or bicyclic ring selected from the group consisting of cycloalkyl, cycloalkenyl, heterocycle, heteroaryl and aryl; wherein each Z is independently unsubstituted or substituted with 1, 2, 3 or 4 substituents selected from the group consisting of oxo, alkyl, haloalkyl, halogen, —NO$_2$, —CN, —OH, alkoxy, haloalkoxy, hydroxyalkyl, —NH$_2$, —N(H)(alkyl), —N(alkyl)$_2$, —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl), —S(O)$_2$N(alkyl)$_2$, R$_E$, and —(CR$^{1a}$R$^{1b}$)$_q$—R$_E$.

2. The method of claim 1 wherein the disorder is bladder overactivity.

3. The method of claim 1 wherein the disorder is urinary incontinence.

4. The method of claim 1 wherein the disorder is pain.

5. The method of claim 1 wherein the disorder is inflammatory hyperalgesia.

* * * * *